(12) United States Patent
Pollner

(10) Patent No.: US 6,346,384 B1
(45) Date of Patent: Feb. 12, 2002

(54) REAL-TIME MONITORING OF PCR USING LOCI

(75) Inventor: Reinhold B. Pollner, San Diego, CA (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 09/536,936

(22) Filed: Mar. 27, 2000

(51) Int. Cl.$^7$ ................................................ C12Q 1/68
(52) U.S. Cl. .................. 435/6; 435/5; 435/6; 435/91.1; 435/91.2; 536/24.3; 536/24.32; 935/77; 935/78
(58) Field of Search .............................. 435/6, 5, 91.1, 435/91.2; 536/24.3, 24.32; 935/77, 78

(56) References Cited

U.S. PATENT DOCUMENTS

| | | |
|---|---|---|
| 5,270,184 A | 12/1993 | Walker et al. |
| 5,395,752 A | 3/1995 | Law et al. |
| 5,427,930 A | 6/1995 | Birkenmeyer et al. |
| 5,547,861 A | 8/1996 | Nadeau et al. |
| 5,593,867 A | 1/1997 | Walker et al. |
| 5,672,475 A | 9/1997 | Lee et al. |
| 5,702,887 A | 12/1997 | Law et al. |
| 5,800,996 A | 9/1998 | Lee et al. |
| 5,853,990 A * | 12/1998 | Winger et al. .................. 435/6 |
| 5,863,727 A | 1/1999 | Lee et al. |
| 5,879,894 A | 3/1999 | Law et al. |
| 6,063,574 A * | 5/2000 | Bronstein et al. ............... 435/6 |

FOREIGN PATENT DOCUMENTS

EP 0515194 * 11/1992

OTHER PUBLICATIONS

Erickson, "Expression in *Escherichia Coli* of the Thermostable DNA Polymerase From *Pyrococcus Furiosus*," Protein Expr. Purif., vol. 11 [2], (1997), pp. 179–84 (Abstract Only).
Heid, et al., "Real Time Quantitative PCR," Genome Research, vol. 6, (1996), pp. 986–994.
Ullman, et al., "Luminescent Oxygen Channeling Immunoassay: Measurement of Particle Binding Kinetics by Chemiluminescence," Proc. Nat'l. Acad. Sci. USA, vol. 91 [12], (1994), pp. 5426–30 (Abstract Only).
Ullman, et al., "Luminescent Oxygen Channeling Assay (LOCI): Sensitive, Broadly Applicable Homogeneous Immunoassay Method," Clin. Chem., vol. 42 [9], (1996), pp. 1518–1526 (Abstract Only).

* cited by examiner

*Primary Examiner*—W. Gary Jones
*Assistant Examiner*—Janell E. Taylor
(74) *Attorney, Agent, or Firm*—McDonnell Boehnen Hulbert & Berghoff; Patrick G Gattari

(57) ABSTRACT

The current invention relates to the use of luminescent oxygen channeling immunoassay ("LOCI") technology to monitor amplification reactions, especially polymerase chain reactions ("PCR"). More specifically, the current invention involves the use of LOCI to measure the kinetics of a PCR reaction in an all-in-one assay format in order to quantitatively and qualitatively detect a target polynucleotide.

20 Claims, 8 Drawing Sheets

SEQUENCE LISTING

<160> NUMBER OF SEQ ID NOS: 11

<210> SEQ ID NO 1
<211> LENGTH: 518
<212> TYPE: DNA
<213> ORGANISM: Chlamydia trachomatis plasmid pLGV440 amplified sequence

<400> SEQUENCE: 1

```
ggacaaatcg tatctcgggt taatgttgca tgatgcttta tcaaatgaca agcttagatc      60
cgtttctcat acggttttcc tcgatgattt gagcgtgtgt agcgctgaag aaaatttgag     120
taatttcatt ttccgctcgt ttaatgagta caatgaaaat ccattgcgta gatctccgtt     180
tctattgctt gagcgtataa agggaaggct tgacagtgct atagcaaaga cttttctat     240 tcgcagcgct agaggccggt ctatttatga tatattctca cagtcagaaa ttggagtgct     300
ggctcgtata aaaaaaagac gagcaacgtt ctctgagaat caaaattctt tctttgatgc     360
```

```
cttcccaaca ggatacaagg atattgatga taaaggagtt atcttagcta aaggtaatttt    420 cgtgattata gcagctaggc catctatagg gaaaactgct ttagctatag acatggcgat    480
aaatcttgcg gttactcaac agcgtagagt tggtttcc                            518

<210> SEQ ID NO 2
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 2
ggacaaatcg tatctcgggt taat                                            24

<210> SEQ ID NO 3
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 3
ggaaaccaac tctacgctgt t                                               21

<210> SEQ ID NO 4
<211> LENGTH: 42
<212> TYPE: DNA
<213> ORGANISM: Artificial Sequence
<220> FEATURE:
<223> OTHER INFORMATION: oligonucleotide probe

<400> SEQUENCE: 4
cgctgcgaat agaaaagtc catttttttt tttttttttt tt                         42

<210> SEQ ID NO 5
<211> LENGTH: 42
<212> TYPE: DNA
<213> ORGANISM: Artificial Sequence
<220> FEATURE:
<223> OTHER INFORMATION: Oligonucleotide probe containing inosine
<221> NAME/KEY: misc_feature
<222> LOCATION: (2)...(2)
<223> OTHER INFORMATION: n = inosine
<221> NAME/KEY: misc_feature
<222> LOCATION: (5)...(5)
<223> OTHER INFORMATION: n = inosine
<221> NAME/KEY: misc_feature
<222> LOCATION: (7)...(7)
<223> OTHER INFORMATION: n = inosine
<221> NAME/KEY: misc_feature
<222> LOCATION: (12)...(12)
<223> OTHER INFORMATION: n = inosine
<221> NAME/KEY: misc_feature
<222> LOCATION: (18)...(18)
<223> OTHER INFORMATION: n = inosine

<400> SEQUENCE: 5
cnctncnaat anaaaaantc catttttttt tttttttttt tt                        42

<210> SEQ ID NO 6
<211> LENGTH: 41
<212> TYPE: DNA
<213> ORGANISM: Artificial Sequence
<220> FEATURE:
<223> OTHER INFORMATION: oligonucleotide probe

<400> SEQUENCE: 6
```

```
tacttactta cttacttact gcctagctgc tataatcacg a                    41
```

<210> SEQ ID NO 7
<211> LENGTH: 40
<212> TYPE: DNA
<213> ORGANISM: Artificial Sequence
<220> FEATURE:
<223> OTHER INFORMATION: oligonucleotide probe
<400> SEQUENCE: 7

```
ctcacagtca gaaattggag tacttactta cttacttact                      40
```

<210> SEQ ID NO 8
<211> LENGTH: 42
<212> TYPE: DNA
<213> ORGANISM: Artificial Sequence
<220> FEATURE:
<223> OTHER INFORMATION: oligonucleotide probe
<400> SEQUENCE: 8

```
tttttttttt tttttttttt agactttttc tattcgcagc gc                   42
```

<210> SEQ ID NO 9
<211> LENGTH: 42
<212> TYPE: DNA
<213> ORGANISM: Artificial Sequence
<220> FEATURE:
<223> OTHER INFORMATION: oligonucleotide probe containing inosine
<221> NAME/KEY: misc_feature
<222> LOCATION: (22)...(22)
<223> OTHER INFORMATION: n = inosine
<221> NAME/KEY: misc_feature
<222> LOCATION: (36)...(36)
<223> OTHER INFORMATION: n = inosine
<221> NAME/KEY: misc_feature
<222> LOCATION: (39)...(39)
<223> OTHER INFORMATION: n = inosine
<221> NAME/KEY: misc_feature
<222> LOCATION: (41)...(41)
<223> OTHER INFORMATION: n = inosine
<400> SEQUENCE: 9

```
tttttttttt tttttttttt anactttttc tattcncanc nc                   42
```

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide attached to beads
<400> SEQUENCE: 10

```
agtaagtaag taagtaagta agta                                       24
```

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide attached to beads
<400> SEQUENCE: 11

```
aaaaaaaaaa aaaaaaaaaa aaaa                                       24
```

Real-Time Monitoring of PCR Using LOCI

REAL-TIME MONITORING OF PCR USING LOCI

FIELD OF THE INVENTION

This invention relates to methods for determining the presence of a target polynucleotide in a sample. In particular, this invention relates to methods for determining the presence of a target polynucleotide by real-time monitoring of an amplification reaction, preferably the polymerase chain reaction (PCR) using luminescent oxygen channeling immunoassay (LOCI) technology.

BACKGROUND OF THE INVENTION

The sensitive detection of nucleic acids in a clinical sample opened a new era in the diagnosis of infectious diseases and other fields. Powerful nucleic acid amplification and detection methods are available which allow the detection of very small copy numbers of target polynucleotides. Tremendous progress has been made concerning the qualitative detection of nucleic acids, but the quantitative detection is still a challenge for the existing methods, especially for amplification methods based on the exponential amplification of a target polynucleotide. The best known amplification method of this type is the polymerase chain reaction (PCR). U.S. Pat No. 4,683,195; U.S. Pat No. 4,683,202.

Nucleic acids in a sample are usually first amplified by the amplification method and subsequently detected by the detection method. This sequential approach is based on a single end-point measurement after the amplification reaction is completed. The amount of amplified product observed at the end of the reaction is very sensitive to slight variations in reaction components because the amplification reaction is typically exponential. Therefore, the accuracy and precision of quantitative analysis using endpoint measurements is poor. Furthermore, endpoint measurements can produce a hook effect whereby high concentrations of a target polynucleotide to be amplified yield inaccurately low values.

In contrast to end-point determinations of amplified polynucleotides, real-time monitoring of amplification reaction product generation offers the possibility of better precision and accuracy in quantitative measurements because the measurements are taken during the exponential phase of the amplification process. In contrast to classical end-point measurements, multiple measurements are taken during real-time monitoring. During the exponential phase of the amplification process, none of the reaction components are limiting, and therefore the affect on accuracy of reaching a maximum signal are eliminated. Real-time monitoring of PCR is based on kinetic measurements offering a better and a more complete picture of the PCR process. A number of real-time monitoring methods have been developed, however the methods use fluorescent signals in all cases. This limits the earliest possible detection of amplifying DNA (RNA) because of the presence of unquenched or background fluorescence. The LOCI signal can be detected well before the fluorescent signal of, for instance, Roche's Taq-Man® fluorescent signal. See Heid et al., (1996) *Genome Res.,* Vol. 6(10), pp. 986–994.

Nadau et al., U.S. Pat. No. 5,547,861 and Walker et al. U.S. Pat. Nos. 5,593,867 and 5,270,184, disclose a method for amplifying a target polynucleotide sequence called strand displacement amplification ("SDA") and methods for detecting amplification products, including a real-time detection method using fluorescence polarization. In SDA temperature cycling is not required. Instead, the method relies on the ability of restriction enzymes to nick hemimodified DNA and relies on DNA polymerase to synthesize a complementary polynucleotide strand from the nick. Detection systems developed for SDA utilize displacement of a fluorescently-labeled detector probe DNA for real-time monitoring of the amplification reaction. A possible disadvantage of this system is that the probe is also a primer and any false priming ("mispriming") of this probe could lead to false positive signal generation. In contrast, the LOCI probes used herein are blocked at the 3' terminal end and cannot be primers.

Numerous dyes have been developed for the detection of nucleic acids to detect a target polynucleotide after it has been amplified. For example, L. Lee et al., U.S. Pat. Nos. 5,863,727 and 5,800,996, describe fluorescent energy-transfer dyes, linkers for synthesizing these dyes, and methods that utilize the dyes. The patents describe the use of the dyes in nucleic acid reactions, including use of the dyes to detect the products of PCR reactions, after the end-point of a reaction and separation by electrophoresis. U.S. Pat. No. 5,863,727 col. 46 line 54. These patents do not disclose the used of the dyes in real-time monitoring of amplification products.

Chemiluminescent dyes, such as luminol and acridinium, and detection systems have been developed which offer the advantage of increased sensitivity over fluorescent systems. M. Lee et al., U.S. Pat No. 5,672,475 ('475 patent), disclose a method for performing end-point measurements of two substances, which theoretically could be polynucleotides, using two chemiluminescent conjugates. An essential feature of the invention of the '475 patent is that each chemiluminescent molecule, eg. luminol and acridinium, is activated under a different set of conditions. The assay disclosed in the '475 patent cannot be used to measure PCR reaction kinetics because the reactions require a separation step to remove unbound labeled conjugate, and therefore are not amenable to an all-in-one-tube assay. In addition, the assay method cannot be used in kinetic measurements of PCR reactions because the measurements require substantial changes in the reaction mixture to activate the chemiluminescent label, which are likely to affect the PCR reaction.

Law et al. U.S. Pat. Nos. 5,879,894, 5,395,752, and 5,702,887 ("Law patents") describe test methods and long-emission wavelength chemiluminescent compounds for detecting two test substances in a single assay. U.S. Pat. No. 5,702,887 briefly mentions the use of two chemiluminescent compounds as labels in an amplification assay such as polymerase chain reaction ("PCR") (Col. 42, lines 31–57). However, although the disclosure indicates that the method could be used to quantitatively measure PCR products, it does not disclose the use of the method to make kinetic measurements of PCR reactions. In fact, the Law patents provide no examples of assays using the disclosed chemiluminescent compounds to measure polynucleotides. Luminescent oxygen channeling Immunoassays (LOCI) have been developed which offer the ability to measure large analytes, such as polynucleotides, with increased sensitivity in a homogeneous or heterogeneous format without the need of adding chemical reagents or heating the reaction to activate the luminescent compounds. U.S. Pat. No. 5,340,716, (Ullman, et al. 1994) (incorporated herein by reference). In LOCI a group which is bound to a specific binding pair member, such as a polynucleotide, is photochemically activated to a luminescent product and is used as a labeled reagent in assays for detection of an analyte, such as a target polynucleotide. The photochemical activation occurs by reaction with singlet oxygen that is generated by photochemical activation of a sensitizer. In the assay protocol the components are combined and the light produced after irradiation of the luminescent product is a function of analyte concentration.

The LOCI method was designed for the analysis of nucleotides in an end-point hybridization reaction. No study has suggested the use of LOCI in real-time monitoring of amplification reactions. It was possible that the kinetics of LOCI hybridization reactions, which involve hybridizations involving bead-coupled probes would be too slow to allow monitoring a PCR reaction. Moreover, the deleterious effect of singlet oxygen on DNA probes makes it problematic that LOCI utilizing a DNA probe would be effective after numerous, repeated illuminations. Finally, temperatures which allow formation of the LOCI complex on target DNA could have allowed unacceptable levels of mispriming, but this is not the case.

There remains a need for an assay method that utilizes an amplification reaction and that can be used for sensitive qualitative and quantitative measurements of a target polynucleotide. More specifically there remains a need for an assay method with the sensitivity of chemiluminescent detection of an amplification product, a wide dynamic range, and good precision and accuracy. To accomplish this, there remains a need for a detection method with rapid incubation and signal generation time to allow the real-time monitoring of an amplification reaction. Finally, there remains a need for an assay which can measure a target polynucleotide in an amplification reaction without a high-dose hook effect.

The current invention relates to the use of LOCI as the detection technology to monitor amplification reactions such as the polymerase chain reaction ("PCR"), in an all-in-one-tube format. More specifically, the current invention involves the use of LOCI to measure the kinetics of a PCR reaction in an all-in-one assay format in order to quantitatively and qualitatively detect a target polynucleotide. The invention has the advantages of the sensitivity of chemiluminescence coupled with rapid signal generation to allow multiple measurements to be taken during the linear phase of a PCR reaction. This provides a more complete picture of the amplification process and sensitive qualitative and quantitative detection of nucleic acids with improved precision, accuracy, and a wider dynamic range.

SUMMARY OF THE INVENTION

The current invention relates to the use of luminescent oxygen channeling immunoassay ("LOCI") technology to monitor amplification reactions, especially polymerase chain reactions ("PCR"). More specifically, the current invention involves the use of LOCI to measure the kinetics of a PCR reaction in an all-in-one assay format in order to quantitatively and qualitatively detect a target polynucleotide.

One embodiment of the invention is directed to a method for detecting the presence of a target polynucleotide in a sample comprising: (A) providing a reaction and detection mixture comprising in combination: (1) a sample; (2) a nucleic acid amplification system; and (3) a chemiluminescent detection system comprising a sensitizer capable of indirectly binding to the target polynucleotide and capable of generating singlet oxygen upon irradiation with light and a singlet-oxygen activatable chemiluminescent compound capable of indirectly binding to the amplified target nucleic acid; (B) amplifying said target polynucleotide through at least one amplification cycle; (C) allowing the indirect binding of said chemiluminescent compound and said sensitizer to said amplified target polynucleotide; (D) activating the sensitizer, wherein said activation of the sensitizer bound to the target polynucleotide causes the activation of said chemiluminescent compound bound to the target polynucleotide; and (E) determining the amount of luminescence generated by the activated chemiluminescent compound; (F) optionally repeating steps B-E; and (G) detecting the presence of said target polynucleotide by analyzing the amount of luminescence determined after at least one amplification cycle. Preferably, the sensitizer is a photosensitizer and the activation of the sensitizer comprises irradiation with light.

In another embodiment of the invention, the target polynucleotide comprises first and second complimentary strands; and the nucleic acid amplification system comprises: (1) a thermostable DNA polymerase; (2) 2' deoxynucleoside-5'-triphosphates; (3) a forward-primer capable of binding to the first complimentary strand; and (4) a reverse-primer capable of binding to the second complimentary strand in a position that will direct DNA synthesis toward the site of annealing of the forward-priming oligonucleotide. The amplification system preferably utilizes the polymerase amplification reaction. If desired, thermal labile antibody against the thermal stable DNA polymerase may be used in a "hot start" amplification reaction.

In yet another embodiment of the invention, the chemiluminescent detection system further comprises: (i) a first linking oligonucleotide capable of binding to both the target polynucleotide and a chemiluminescer-associated oligonucleotide; and (ii) a second linking oligonucleotide capable of binding to both the target polynucleotide and a sensitizer-associated oligonucleotide. If desired, guanosine residues may be replaced with inosine residues in one or both of the first and second linking probes. The sensitizer and sensitizer-associated oligonucleotide are associated with a first solid support while the singlet-oxygen activatable chemiluminescent compound and the chemiluminescer-associated oligonucleotide are associated with a second solid support. Preferably, the first and second solid support are beads and the acceptor beads comprise thioxene, anthracene, and rubrene.

In a further embodiment of the invention, a method for quantifying the amount of target polynucleotide in a sample is provided. The amount of luminescence is related to the amount of target polynucleotide in the sample. The luminescence determinations are made during an exponential phase of the amplification process and involve (a) determining a threshold cycle number at which the luminescence generated from amplification of the target polynucleotide in a sample reaches a fixed threshold value above a baseline value; and (b) calculating the quantity of the target polynucleotide in the sample by comparing the threshold cycle number determined for the target polynucleotide in a sample with the threshold cycle number determined for target polynucleotides of known amounts in standard solutions.

In yet another embodiment of the invention, a method is provided for detecting the presence of a target polynucleotide in a sample, the target polynucleotide comprising a first and a second complimentary strand. The method comprises (a) providing a reaction and detection mixture comprising in combination: (1) a sample, (2) a thermostable DNA polymerase, (3) 2' deoxynucleoside-5'-triphosphates, (4) a forward-primer capable of binding to the first complimentary strand, (5) a reverse-primer capable of binding to the second complimentary strand in a position that will direct DNA synthesis toward the site of annealing of the forward-priming oligonucleotide, and (6) a chemiluminescent detection system comprising a photosensitizer capable of indirectly binding to the target polynucleotide and capable of generating singlet oxygen upon irradiation with light and a singlet-oxygen activatable chemiluminescent compound capable of indirectly binding to the amplified target nucleic acid; (b) denaturing said target polynucleotide for an initial denaturation period; (c) denaturing said target polynucleotide for a cycle denaturation period; (d) incubating the reaction and detection mixture to allow indirect binding of said chemiluminescent compound and said photosensitizer to said amplified target polynucleotide; (e) irradiating the photosensitizer with light, wherein said irradiation causes the activation of said chemiluminescent compound bound to the target polynucleotide by the sensitizer bound to the target polynucleotide; and (f) determining the amount of luminescence generated by the activated chemiluminescent compound; (g) annealing said forward priming and reverse priming oligonucleotides to the target polynucleotide; (h) synthesizing polynucleotide strands complementary to said first and second complementary strands of said target polynucleotide, said synthesis being catalyzed by the thermostable DNA polymerase; (i) optionally repeating steps C—H; and (j) detecting the presence of said target polynucleotide by analyzing the amount of luminescence determined after at least one amplification cycle.

These and other embodiments of the invention will become apparent in light of the detailed description below.

DETAILED DESCRIPTION OF THE INVENTION

Figure 1:
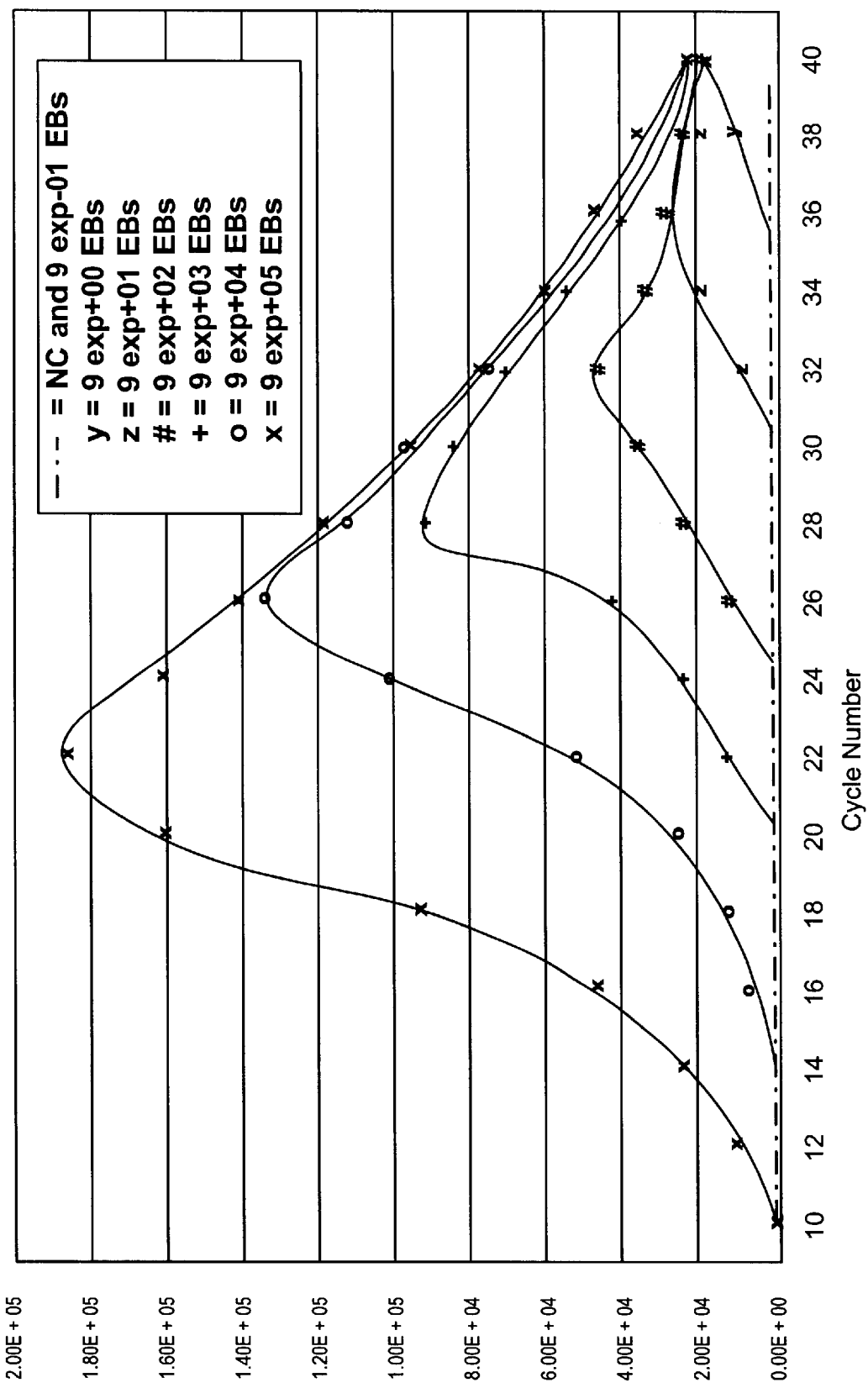
FIG. 1 is a plot of light emission intensity in relative light units versus cycle number where the sample contains different amounts (elementary bodies) of a *Chlamydia trachomatis* DNA.

Definitions:

"Beads" refers to a particulate water-suspendible water-insoluble polymeric material usually having particle dimensions of 20 nm to 20 mm, more preferably 100 to 1000 nm in diameter. The bead is preferably latex that is frequently a substituted polyethylene such as the following: polystirene-butadiene, polyacrylamide polystirene, polystirene with amino groups, poly-acrylic acid, polymethacrylic acid, acrylonitrile-butadiene, stirene copolymers, polyvinyl acetate-acrylate, polyvinyl pyridine, vinyl-chloride acrylate copolymers, and the like. Non-crosslinked polymers of stirene and carboxylated stirene or stirene functionalized with other active groups such as amino, hydroxyl, halo and the like are preferred. Frequently, copolymers of substituted stirenes with dienes such as butadiene will be used.

The association of the photosensitizer or SACC with beads utilized in the present invention may involve incorporation during formation of the particles by polymerization but will usually involve incorporation into preformed particles, usually by noncovalent dissolution into the particles. Usually a solution of the SACC or photosensitizer will be employed. Solvents that may be utilized include alcohols (including ethanol), ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the compounds into the particles and are particularly suitable. The solvents may be used singly or in combination. Particularly preferred solvents for incorporating a photosensitizer are those that will not quench the triplet excited state of the photosensitizer either because of their intrinsic properties or because they can subsequently be removed from the particles by virtue of their ability to be dissolved in a solvent such as water that is insoluble in the particles. Aromatic solvents are preferred, and generally solvents that are soluble in the particle. For incorporating SACCs in particles a solvent should be selected that does not interfere with the fluorescence of the SACCs formed because of their intrinsic properties or ability to be removed from the particles. Frequently, aromatic solvents will also be preferred. Typical aromatic solvents include dibutylphthalate, benzonitrile, naphthonitrile, dioctylterephthalate, dichlorobenzene, diphenylether, dimethoxybenzene, etc.

Except when the photosensitizer or SACC compound is to be covalently bound to the beads, it will usually be preferable to use electronically neutral photosensitizers or SACCs. It is preferable that the liquid medium selected does not soften the polymer beads to the point of stickiness. A preferred technique comprises suspending the selected beads in a liquid medium in which the photosensitizer or SACC has at least limited solubility. Preferably, the concentrations of the photosensitizer and SACC in the liquid media will be selected to provide beads that have the highest efficiency of singlet oxygen formation and highest quantum yield of emission from the photoactive indicator so formed in the media. However, less concentrated solutions will sometimes be preferred. Distortion or dissolution of the particles in the solvent can be prevented by adding a miscible cosolvent in which the particles are insoluble.

Generally, the temperature employed during the procedure will be chosen to maximize the singlet oxygen formation ability of the photosensitizer-labeled beads and the quantum yield of the photoactive indicator so formed from the SACC-labelled particles with the proviso that the particles should not become aggregated at the selected temperature. Elevated temperatures are normally employed. The temperatures for the procedure will generally range from 20° C. to 200° C., more usually from 50° C. to 170° C. It has been observed that some compounds that are nearly insoluble in water at room temperature, are soluble in, for example, low molecular weight alcohols, such as ethanol and ethylene glycol and the like, at elevated temperatures. Carboxylated modified beads have been shown to tolerate low molecular weight alcohols at such temperatures.

An oligonucleotide may be physically adsorbed on the surface of the bead or may be covalently bonded to the particle. In cases wherein the oligonucleotide is only weakly bound to the surface of the latex particle, the binding may in certain cases be unable to endure particle-to-particle shear forces encountered during incubation and washings. Therefore, it is usually preferable to covalently bond oligonucleotides to the beads under conditions that will minimize adsorption. This may be accomplished by chemically activating the surface of the latex bead. For example, the N-hydroxysuccinimide ester of surface carboxyl groups can be formed and the activated beads to reduce nonspecific binding of assay components to the bead surface are then contacted with a linker having amino groups that will react with the ester groups. The linker will usually be selected to reduce nonspecific binding of assay components to the particle surface and will preferably provide suitable functionality for both attachment to the latex bead and attachment of the oligonucleotide. Suitable materials include maleimidated aminodextran (MAD), polylysine, aminosaccharides, and the like. MAD can be prepared as described by Hubert, et al., *Proc. Natl. Acad. Sci.,* 75(7), 3143, 1978.

"Linking oligonucleotide" is an oligonucleotide capable of binding to both the amplified target polynucleotide and a chemiluminescer-associated oligonucleotide. Preferably, two linking oligonucleotides are contained in a reaction, one which binds both an oligonucleotide associated with an acceptor and the target polynucleotide, and one which binds an oligonucleotide associated with a sensitizer and the target polynucleotide. Preferably for the linking oligonucleotide capable of binding to the oligonucleotide associated with the sensitizer, guanosine residues are replaced by nucleotides that are not vulnerable to singlet oxygen, most preferably inosine.

"Photosensitizer" refers to a molecule which, for the purposes of this invention, can be excited to a metastable state, usually a triplet state, which in the proximity of molecular oxygen can directly or indirectly transfer its energy to the oxygen with concomitant excitation of the oxygen to a highly reactive excited state of oxygen often referred to as singlet oxygen or $^1O_2$. The photosensitizer will usually be excited by the absorption of light or by an energy transfer from an excited state of a suitable donor but may also be excited by chemiexcitation, electrochemical activation or by other means. Usually excitation of the photosensitizer will be caused by irradiation with light from an external source. The photosensitizers of this invention will usually have an absorption maximum in the wavelength range of 250–1100 nm, preferably 300–1000 nm, and more preferably 450–950 nm, with an extinction coefficient at its absorbance maximum greater than 500 $M^{-1}cm^{-1}$, preferably at least 5000 $M^{-1}cm^{-1}$, more preferably at least 50,000 $M^{-1}cm^{-1}$. The lifetime of the excited state, usually a triplet state, produced following absorption of light by the photosensitizer will usually be at least 100 nsec, preferably at least 1 microsecond in the absence of oxygen. In general, the lifetime must be sufficiently long to permit the energy transfer to oxygen, which will normally be present at concentrations in the range of $10^{-5}$ to $10^{-2}$M (depending on the medium). The excited state of the photosensitizer will usually have a different spin quantum number (S) than its ground state and will usually be in a triplet (S=1) state when, as is usually the case, the ground state is a singlet (S=0). Preferably, the photosensitizer will have a high intersystem crossing yield. That is, excitation of a photosensitizer will produce the long lived state (usually triplet) with an efficiency of at least 10%, desirably at least 40%, preferably greater than 80%. The photosensitizer will usually be at most weakly fluorescent under the assay conditions (quantum yield usually less than 0.5, preferably less that 0.1).

Photosensitizers of the instant invention are relatively photostable and will not react efficiently with the singlet molecular oxygen so generated. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they will frequently have polyaromatic structures. Typical photosensitizers include ketones such as benzophenone and 9-thioxanthone; xanthenes such as eosin and rose bengal; polyaromatic compounds such as buckminsterfullerene and 9,10-dibromoanthracene; porphyrins including metalloporphyrins such as hematoporphyrin and chlorophylis; oxazines; cyanines; squarate dyes; phthalocyanines; naphthalocyanines; merocyanines; thiazines such as methylene blue, etc., and derivatives of these compounds substituted by an organic group for enhancing intersystem crossing and rendering such compounds more lipophilic or more hydrophilic and/or as attaching groups for attachment, for example, to a polynucleotide. Examples of other photosensitizers that may be utilized in the present invention are those that have the above properties and are enumerated in N. J. Turro, "Molecular Photochemistry", page 132, W. A. Benjamin Inc., N.Y. 1965.

"Polynucleotide" refers to a compound or composition which is a polymeric nucleotide having in the natural state about 6 to 500,000 or more nucleotides and having in the isolated state about 6 to 50,000 or more nucleotides, usually about 6 to 20,000 nucleotides, more frequently 6 to 10,000 nucleotides. The term "polynucleotide" includes oligonucleotides and nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide is typically composed of the nucleotides adenosine, guanosine, adenosine, and thymidine. However, the polynucleotide can be composed of other nucleotides, for example de-aza guanosine or preferably inosine, as long as they do not destroy the binding of the polynucleotide to its target.

"Primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an inducing agent such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method. For example, for diagnostics applications, depending on the complexity of the target sequence, the oligonucleotide primer typically contains 15–25 or more nucleotides, although it may contain fewer nucleotides.

The primers herein are selected to be "substantially" complementary to the different strands of the target polynucleotide. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer.

"Sensitizer" refers to a molecule which, for the purposes of this invention, can generate a reactive oxygen species, preferably singlet oxygen. Examples of sensitizers include photosensitizers and enzymes. Enzymes which function as photosensitizers include haloperoxidases which form singlet oxygen by catalyzing the reaction of a halide-compound, such as a sodium halide, with hydrogen peroxide.

"Singlet-oxygen activatable chemiluminescent compound" (SACC) refers to a photoactivatable substance that undergoes a chemical reaction upon direct or sensitized excitation by light or upon reaction with singlet oxygen to form a metastable reaction product that is capable of decomposition with the simultaneous or subsequent emission of light, usually within the wavelength range of 250 to 1200 nm. The term "photoactivatable" includes "photochemically activatable." SACC's that are preferred in the present invention are those that react with singlet oxygen to form dioxetanes or dioxetanones. The latter are usually electron rich olefins (1). Exemplary of such electron rich olefins are enol ethers, enamines, 9-alkylidene-N-alkylacridans, arylvinylethers, dioxenes, arylimidazoles, 9-alkylidene-xanthanes and lucigenin. Other compounds that are included in the term "SACC" include luminol and other phthalhydrazides and chemiluminescent compounds that are protected from undergoing a chemiluminescent reaction by virtue of their being protected by a photochemically labile protecting group, such compounds including, for example, firefly luciferin, aquaphorin, luminol, etc.

The SACC's of interest will preferably emit at a wavelength above 300 nanometers, preferably above 500 nanometers, and more preferably above 550 nm. Compounds that absorb and emit light at wavelengths beyond the region where the sample components contribute significantly to light absorption will be of particular use in the present invention. The absorbance of serum drops off rapidly above 500 nm and becomes insignificant above 600 nm; therefore, chemiluminescent compounds that emit light above 600 nm are of particular interest. However, chemiluminescent compounds that absorb at shorter wavelengths are useful when interference absorbance of the sample is absent.

In order to avoid autosensitization of the chemiluminescent compound, it is preferable that the chemiluminescent compounds do not absorb light used to excite the photosensitizer. Since it will generally be preferable to excite the sensitizer with light wavelengths longer than 500 nm, it will therefore be desirable that light absorption by the chemiluminescent compound be very low above 500 nm.

Where long wavelength emission from the chemiluminescent compound is desired, a long wavelength emitter such as a pyrene, bound to the chemiluminescent compound can be used. Alternatively, a fluorescent molecule can be included in the medium containing the chemiluminescent compound. Preferred fluorescent molecules will be excited by the activated chemiluminescent compound and emit at a wavelength longer than the emission wavelength of the chemiluminescent compound, usually greater that 550 nm. It is usually also desirable that the fluorescent molecules do not absorb at the wavelengths of light used to activate the photosensitizer. Examples of useful dyes include rhodamine, ethidium, dansyl, $Eu(fod)_3$, $Eu(TTA)_3$, $Ru(bpy)_3^{++}$ (wherein bpy=2,2'-dipyridyl, etc.), rubene, bispehenethylhyl anthracene, Nile red, Texas red, amino-coumarins, umbelliferones, squarine dyes, and fluorescein. In general these dyes act as acceptors in energy transfer processes and preferably have high fluorescent quantum yields and do not react rapidly with singlet oxygen. They can be incorporated into particles simultaneously with the incorporation of the chemiluminescent compound into the particles.

"Support" or "surface" refers to a surface comprised of porous or non-porous water insoluble material. The surface can have any one of a number of shapes, such as strip, rod, particle, bead, and the like. The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystirene, polymethacrylate, poly (ethylene terephthalate), nylon, poly(vinyl butyrate), etc.; either used by themselves or in conjunction with other materials such as glass available as Bioglass, ceramics, metals, and the like. Natural or synthetic assemblies such as liposomes, lipid vesicles, and cells can also be employed. Preferably, the support is a suspendible particle, more preferably a bead comprised of latex.

Binding of polynucleotides, photosensitizers, and photoactive chemiluminescent compounds to the support or surface may be accomplished by well-known techniques, commonly available in the literature. The surface will usually be polyfunctional or be capable of being polyfunctionalized or be capable of binding a polynucleotide, a photosensitizer, and/or a photoactive chemiluminescent compound and associated fluorescent dyes through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well know and is amply illustrated in the literature. See for example Cautrecasas, *J. Biol. Chem.,* Vol. 245, 3059 (1970). The length of a linking group to the oligonucleotide or sbp member may vary widely, depending upon the nature of the compound being linked, the effect of the distance between the compound being linked and the surface on the specific binding properties and the like.

"Suspendible particles" refers to particles capable of being suspended in water which are at least about 20 nm and not more than about 20 microns, usually at least about 40 nm and less than about 10 microns, preferably from about 0.10 to 2.0 microns in diameter, and which normally have a volume of less than about 4 picoliters. The suspendible particles may be organic or inorganic, swellable or non-swellable, porous or non-porous, preferably of a density approximating water (generally from about 0.7 to about 1.5 g/ml), and composed of material that can be transparent, partially transparent, or opaque. The suspendible particles will usually be charged, preferably negatively charged. The suspendible particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or other lipids such as dialkyl phosphates or natural such as cells and organelles). The suspendible particles may be latex particles or other particles comprised of organic or inorganic polymers; lipid vesicles, e.g., liposomes; phospholipid vesicles; oil droplets; silicon particles; metal sols; cells; and dye crystallites.

If organic, the suspendible particles may be polymers, either addition or condensation polymers, which are readily suspendible in the assay medium. The organic suspendible particles will also be adsorptive or functionalizable so as to bind at their surface a polynucleotide (either directly or indirectly) and to bind at their surface or incorporate within their volume a photosensitizer or a singlet-oxygen activatable chemiluminescent compound and associated dyes.

The suspendible particles can be derived from naturally-occurring materials, naturally-occurring materials which are synthetically modified and synthetic materials. Natural or synthetic assemblies such as lipid bilayers, e.g., liposomes and non-phospholipid vesicles. Among organic polymers of particular interest are polysaccharides, particularly cross-linked polysaccharides, such as agarose, which is available as Sepharose, dextran, available as Sephadex and Sephacryl, cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, selenium, and other metals. Suspendible particles may also be dispersed water insoluble dyes such as porphyrins, phthalocyanines, etc., which may also act as photosensitizers. Suspendible particles may also include diatoms, cells, viral particles, oil droplets, fat particles such as alkyl triglycerides, magnetosomes, cell nuclei and the like.

Where non-polymeric particles are used, the particle size may be varied by breaking larger particles into smaller particles by mechanical means, such as grinding, sonication, agitation, etc.

Like the surface or support defined above, the suspendible particles will usually be polyfunctional or be capable of being polyfunctionalized or be capable of being bound to a polynucleotide, photosensitizer, or SACC through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of a polynucleotide, chemiluminescent compound or photosensitizer to the particle is employed, the manner of linking is well known and is amply illustrated in the literature. See for example Cautrecasas, *J. Biol. Chem.,* 245:3059 (1970). The length of a linking group may vary widely, depending upon the nature of the compound being linked, the nature of the particle, the effect of the distance between the compound being linked and the particle on the binding of sbp members and the analyte and the like.

The photosensitizer and/or SACC can be chosen to dissolve in, or covalently bind to suspendible particles. When noncovalently bound, the compounds and the particles may be hydrophobic to reduce the ability of the compounds to dissociate from the particles, called leakage, and to associate with the same particle. Preferably, these compounds are covalently bound to separate particles. When either one or both of the compounds are covalently bound to particles each compound may be either hydrophilic or hydrophobic.

The number of photosensitizer or singlet-oxygen activatable chemiluminscent compound molecules associated with each particle will be at least one and may be sufficiently high so that the particle consists entirely of photosensitizer or SACC molecules. The preferred number of molecules will be selected empirically to provide the highest signal. In general, the more molecules the more photoactive chemiluminescent molecules can potentially be formed, but this must be balanced by a reduction in the fluorescence efficiency. Normally, the concentration of photosensitizer and SACC in the particles will range from $10^{-8}$ to 5M, usually from $10^{-5}$ to $10^{-1}$M, preferably from $10^{-3}$ to $10^{-1}$M. Similar concentrations of the singlet oxygen activatable chemiluminscent compound will be preferred when the compound is incorporated into non-particulate materials. The photosensitizers of the instant invention are preferably relatively non-polar to assure dissolution into a lipophilic member when the photosensitizer is incorporated into a suspendible particle such as an oil droplet, liposome, latex particle, and the like.

"Target polynucleotide" refers to the polynucleotide in a sample of which at least a portion is intended to be amplified by the amplification reaction. Where an amplification reactions that utilize oligonucleotide primers for an extension reaction are used, such as PCR, the target polynucleotide is that nucleotide to which the extension primers are intended to bind.

"Threshold cycle number" is an amplification cycle number at which point chemiluminescence intensity reaches or exceeds a certain level.

Method of the Present Invention

The general method of the invention involves an all-in-one assay for detecting a target polynucleotide in a sample during amplification of the polynucleotide, preferably by the polymerase chain reaction (PCR). Detection is accomplished by monitoring amplification of the target DNA using a chemiluminescent system, preferably the LOCI system. Typically, the method commences with at least one cycle of amplification of the target polynucleotide. After at least one cycle of amplification, LOCI components are allowed to bind to the target polynucleotide and a measurement of luminescence is taken. Additional luminescence measurements are taken after subsequent cycles. These measurements are then analyzed and used to determine the presence of the target polynucleotide.

Amplification of the target polynucleotide is carried out by an amplification method. A preferred amplification method is the polymerase chain reaction. Mullis, U.S. Pat. No. 4,683,202 (1987). However, other amplification methods are known, including the ligase chain reaction. EP-A-320 308; U.S. Pat. No. 5,427,930. The requirements of the nucleic acid amplification method are that it is capable of amplifying the target polynucleotide many times and the method can be paused so that the amplified product can be detected during the amplification process. Finally, the amplification method cannot destroy the detection system during rounds of amplification.

The nucleic acid amplification method typically occurs through a repetitive series of cycles, preferably temperature cycles. The first step in the amplification process is typically separation of the two strands of the polynucleotide so that they can be used as templates, unless the target polynucleotide is single-stranded wherein separation is not necessary. Another exception to the usual first step separation occurs when the target polynucleotide is RNA instead of DNA. In this situation a reverse transcriptase is typically used to synthesize a DNA strand from the RNA template before the strand separation step. The strand separation can be accomplished by any suitable method including physical, chemical or enzymatic means. One preferred physical method of separating the strands of the nucleic acid involves heating the nucleic acid until it is denatured. Typical heat denaturation may involve temperatures ranging from about 80 C to 105 C for times ranging from about 1 to 10 minutes. Other methods of strand separation are known in the art including separation using enzymes known as helicases. Cold Spring Harbor Symposia on Quantitative Biology, Vol. XLIII "DNA: Replication and Recombination" (New York: Cold Spring Harbor Laboratory, 1978), B. Kuhn et al., "DNA Helicases", pp. 63–67; C; Radding, *Ann. Rev. Genetics,* 16: 405–37 (1982).

When the complementary strands of the target polynucleotide are separated, whether the nucleic acid was originally double or single stranded, the strands are ready to be used as a template for the synthesis of additional polynucleotide strands. This synthesis can be performed using any suitable method. Generally it occurs in a buffered aqueous solution, preferably at a pH of 7–9, most preferably about 8. Preferably, a molar excess of two oligonucleotide primers, a forward primer and a reverse primer, is added to the buffer containing the separated template strands. It is understood, however, that the amount of complementary strand may not be known, for example if the process herein is used for target polynucleotides of unknown concentrations in patient samples. As a practical matter, however, the amount of primer added will generally be in molar excess over the amount of complementary strand (template). The deoxyribonucleoside triphosphates dATP, dCTP, dGTP and dTTP and an agent for inducing or catalyzing the primer extension are also added to the synthesis mixture in adequate amounts and the resulting solution is heated to about 90 C–100 C for from about 1 second to 5 minutes, preferably from 10 to 30 seconds, most preferably 15 seconds. The agent for inducing or catalyzing the primer extension reaction is typically a thermostable DNA polymerase of which many are known in the art. Preferably the thermostable polymerase is Taq polymerase, most preferably it is Pfu, the DNA polymerase from *Pyrococcus furiosis,* which has an exceptionally low error rate. After this heating period the solution is allowed to cool to a temperature which allows primer hybridization. The temperature is then typically changed to a temperature that will allow the polymerase-catalyzed primer extension reaction to occur under conditions known in the art. This synthesis reaction may occur at from room temperature up to a temperature above which the inducing agent no longer functions efficiently. The temperature is typically higher than that used for annealing the forward and reverse primers to the template. One of ordinary skill in the art can readily use empirical means to determine the appropriate denaturation and annealing temperatures for any particular amplification reaction mixture and program a thermocycler accordingly. Generally, the synthesis will be initiated at the 3' end of each primer and proceed in the 5' direction along the template strand until synthesis terminates.

The newly synthesized strand and its complementary nucleic acid strand form a double-stranded molecule which is used in succeeding rounds of synthesis by repeating the strand-separation, primer annealing, and extension steps described above. These steps can be repeated as often as needed. The amount of the specific nucleic acid sequence produced will accumulate in an exponential fashion. Therefore, the amplification process includes an exponential phase that typically ends when one or more of the reactants are exhausted.

In one preferred embodiment, a "hot start" method is used to improve specificity. In general, in this preferred but non-essential embodiment at least one component that is essential for polymerization is not present until the reaction is heated to the annealing or extension temperatures. This method, termed "hot start," improves specificity and minimizes the amplification of unspecific DNA. The hot start method also minimizes the formation of "primer-dimers," which are double-stranded PCR products resulting from extension of one primer using the other primer as template. In one embodiment of the hot start method, DNA polymerase can be added to the PCR reaction mixture after both the primer and template are added and the temperature has been increased appropriately. Alternatively, for example, after the temperature has been increased appropriately, the enzyme and primer are added last or the PCR buffer or template plus buffer are added last. Finally, a commercially available wax beads such as PCR Gems® (PE biosystems, Foster City, Calif., USA) may be used in a hot start method. The wax beads melt and form a barrier at the top of the PCR reaction mixture. The enzyme is added to the top of the wax barrier, and thermal cycling is continued wherein the wax melts again and allows mixing of the polymerase with the rest of the mixture and hot start amplification begins.

In other embodiment of the hot start method, thermal stable DNA polymerases which activate upon heating to high temperatures (e.g., above 60 C) may be used. Suitable thermal stable DNA polymerases include the ones described in Roche U.S. Pat. No. 5,677,152. Alternatively, a hot start method could utilize an antibody against the thermal stable DNA polymerase which inactivates the polymerase until the antibody comes off the polymerase at relatively high temperatures. See for instance, Kodak U.S. Pat. No. 5,338,671. Finally, one suitable hot start method for nucleic acid amplification with thermostable polymerase is described in a co-pending patent application Ser. No. 09/233,413, filed Jan. 19, 1999 entitled METHOD FOR CONTROLLING THE EXTENSION OF AN OLIGONUCLEOTIDE and listing Nurith Kurn, Alla Lishanski, Yen Ping Liu and Marc Taylor as inventors. This application is incorporated by reference in its entirety.

In the current invention, a chemiluminescent detection system is utilized to monitor the PCR reaction. The chemiluminescent detection system components are added to the amplification reaction mixture before or during the amplification process. Activation of the chumiluminescent detection system as well as the components of the system themselves must not destroy the amplification process. Therefore, activation of and analysis using the chemiluminescent system must be rapid and must not utilize chemicals that interfere with the amplification process. Preferably, the chemiluminescent system comprises activation of a chemiluminescent molecule by singlet oxygen. Most preferably, the chemiluminescent system comprises LOCI technology.

The chemiluminescene detection system, which preferably comprises a sensitizer and a SACC, must be activated and analyzed between certain steps in the amplification process. In one embodiment, the chemiluminescent detection system is not activated after all of the amplification cycles. The chemiluminescence analysis can be carried out at a variety of temperatures, typically the chemiluminescence analysis is performed at temperatures between 20 C and 75 C, preferably 37 C. The desired temperature range will depend on the length of the probe, bead oligo base pairing, and probe/target base pairing.

In a preferred embodiment, the chemiluminescent detection system comprises he following five steps:

(1) Association of the chemiluminescent components with the target polynucleotide;

(2) Activation of a sensitizer by irradiation with light;

(3) Activation of an SACC through singlet oxygen produced by the activation of the sensitizer;

(4) Detection of the light produced by the activated SACC.

(5) Data reduction of the intensity of light produced by the SACC after certain amplification cycle numbers.

In a first step of the preferred embodiment outlined above, the sensitizer and SACC become associated with the target polynucleotide of the amplification process. This association typically occurs through the binding of linking polynucleotides which anneal to both the target polynucleotide and an oligonucleotide associated with the sensitizer or SACC. Typically, the oligonucleotide associated with the sensitizer or SACC is associated with these groups by being bound to the same solid support as the sensitizer or SACC, preferably the solid support is a suspendable particle, most preferably a latex bead. The association of the chemiluminescent detection system components and the target polynucleotide typically occurs after the separation step in the amplification process. This provides available strands of the target polynucleotide for the binding of linking oligonucleotides. Typically, the linking oligonucleotides is associated with both the target polynucleotide and oligonucleotides associated with the sensitizer or SACC through complementarity of nucleotide sequences.

In a second step of the preferred chemiluminescent detection system, the sensitizer is activated by irradiation with light, preferably to generate singlet oxygen. Typically, this irradiation occurs at between 600 and 800 nm for between 0.1 and 10 seconds. Preferably, this irradiation occurs at 675 nm for 0.1 second.

In a third step of the preferred chemiluminescent detection system, singlet oxygen produced by the sensitizer activates the SACC. This activation is dependent on the presence of target polynucleotide because the sensitizer and SACC must be in close proximity for the singlet oxygen molecule produced by he sensitizer to activate the SACC. Proximity of these components is achieved by the association of the sensitizer and the SACC to the target polynucleotide in the first step of the process. The amount of SACC activated depends on the amount of target polynucleotide present in the sample.

In a fourth step, the activated SACC emits light which is detected and measured. The ability to emit light upon activation is a characteristic of the SACCs of the invention. In a preferred embodiment the SACC comprises thioxene, anthracene, and rubrene which are all associated with the same latex beads. Luminescence of the SACC or chemiluminescent compounds typically is measured by commercially available instruments, e.g., luminometers, well-known in the art. For example, strip readers are commercially available for reading multiple samples more is used to measurement light emitted by the SACC or by other chemiluminescent compounds activated by the SACC.

In a fifth step, the measurements of light emitted by the SACC after a certain number of cycles are translated into a qualitative determination of the presence of the target polynucleotide or a quantitative determination of the amount of target polynucleotide present in the sample. In one embodiment, qualitative determinations are made by comparing the light emitted after various amplification cycles for the sample compared with a control without target polynucleotide. Typically, quantitative determinations involve the generation of a standard curve using measurements taken from samples with known amounts of target polynucleotide. In a preferred embodiment the amount of target polynucleotide in a sample is generated by determining a threshold cycle number at which the luminescence generated from amplification of the target polynucleotide in a sample reaches a fixed threshold value above a baseline value. This cycle number is compared to a standard curve of threshold cycle numbers determined using target polynucleotides of various known concentrations to yield the quantity of target polynucleotide in the sample. Various data reduction techniques including point to point and curve fitting techniques known in the art can be used for this analysis.

The method of the present invention is useful in many of the situations in which PCR is useful, including the analysis of a patient's own genome. In a preferred embodiment of the present invention various infectious diseases, for humans and animals, can be diagnosed by the presence in clinical samples of specific target polynucleotides characteristic of the causative microorganism. These microorganisms include, but are not limited to, bacteria, such as Salmonella, Chlamydia, and Neisseria; viruses, such as the hepatitis viruses and Human Immunodeficiency Virus; and protozoan parasites, such as the Plasmodium responsible for malaria. Preferably the causative microorganism detected by the present method is *Chlamydia trachomatis*. The invention is especially effective in detecting disease-causing microorganisms because it can detect very small numbers of target polynucleotides of the pathogenic organism.

SPECIFIC EXAMPLES

The invention is demonstrated further by the following illustrative examples. The examples are offered by way of illustration and are not intended to limit the invention in any manner. In these examples all percentages are by weight if for solids and by volume if for liquids, and all temperatures are in degrees Celsius unless otherwise noted.

The following abbreviations are used in the Examples:

| | The following abbreviations are used in the Examples: |
|---|---|
| BSA | Bovine serum albumin |
| Ct | *Chlamydia trachomatis* |
| DMF | dimethylformamide |
| DMSO | dimethyl sulfoxide |
| DopTAR | Doped Thioxene/Anthracene/Rubrene-containing beads |
| DTT | dithiothreitol from Sigma Chemical Company, St. Louis, MO. |
| EB | Elementary bodies |
| EDAC | 1-ethyl-3-(3-dimethylaminopropyl)-carbodiimide hydrochloride. |
| EDTA | ethylenediaminetetraacetate dNTPs 2'-deoxynucleoside-5'-triphosphates |
| FWP | Forward primer |
| RevP | Reverse primer |
| HBR | Heterophile Blocking Agent (Scantibodies Laboratory, Inc., Santee, CA) |
| HPLC | high performance liquid chromatography. |
| IHBB | In-house buffer with BSA |
| LC | liquid chromatography |
| LSIMS | fast ion bombardment mass spectroscopy |
| LOCI | Luminescent oxygen channeling immunoassay |
| MES | 2-(N-morpholino) ethane sulfonic acid |
| MOPS | 3-(N-morpholino) propanesulfonic acid |
| NMR | nuclear magnetic resonance spectroscopy |
| PCR | Polymerase chain reaction |
| Pfu/exo- | *Pyrococus furiosus* DNA polymerase/exo- |
| SIAX | Succinimidyl 6-((iodoacetyl)amino) hexanoate |
| SPDP | N-succinimidyl 3-(2-pyridylthio)-propionate. |
| Sulfo-SMCC | N-sulfosuccinimidyl-4-(N-maleimidornethyl) cyclohexane-1-carboxylate |
| TSO | Template switching oligonucleotide |
| TAR | Thioxene/Anthracene/Rubrene |
| TCEP | tris-carboxyethyl phosphine |
| THF | tetrahydrofuran |
| TMSCI | trimethylsilylchloride |
| TRIS | Tris (Hydroxymethyl) Aminoethane |
| Tris HCl | Tris (hydroxymethyl) aminomethane-HCl (a 10X solution) from Bio Whittaker, Walkersville, MD. |
| TRIS | Tris (Hydroxymethyl) Aminoethane |

Example 1
Real-Time Monitoring of PCR Amplification of *Chlamydia trachomatis* DNA Using LOCI as the Detection Technology
A. Preparation of Reagents Acceptor beads (Doped TAR), phthalocyanine sensitizer, and oligonucleotide-loaded beads for PCR/LOCI were prepared for this experiment.

1×IHBB: 50 mM KCI, 4 mm $MgCl_2$ 10 mM Tris-HCI pH 8.3,200 µg/ml BSA.

Parts and percentages recited herein are by weight unless otherwise specified. Temperatures are in degrees centigrade (° C.). Unless indicated otherwise, chemicals were reagent grade and commercially available from sources such as Gibco, (Rockville, Md.), Aldrich Chemical Company (Milwaukee, Wis.) and Sigma Chemical Company (St. Louis, Mo.). All solutions were prepared in water and all reactions were performed under ambient conditions unless otherwise stated.

C-28 thioxene was prepared as described below. 2-Chloro 9,10-bis (phenylethynyl) anthracene (1-CI-BPEA) and rubrene (5,6,11,12-tetraphenyl naphthacene) were purchased from Aldrich Chemical Co. Rubrene was recrystalized from methylene chloride and stored at 4° C. in a brown bottle prior to use. Silicon phthalocyanine was prepared as described below. Carboxylate-modified polystirene (latex) particles were purchased from Seradyn, Inc. The particles were 203±4.0 nm in diameter. The carboxyl parking area was 49.5 angstroms squared (0.09 milliequivalents/g). Solids were 10% (100 mg/ml).

2-ethoxyethanol was from Aldrich Chemical Co. and was redistilled under vacuum. Sodium hydroxide was 0.1 N. Isopropanol, hydrazine, and N-(2,3-epoxypropyl) phthalimide were from Aldrich Chemical Co. N-heptadecylbenzene was from Pfaltz and Bauer. Tween 20 was Surfact-Amps 20 (Pierce Chemical Company, Rockford, Ill.). Acetylated BSA was from Gibco BRL, Gaithersburg, Md. and Kathon was from Rohm and Haas Company, Philadelphia, Pa.

Unless otherwise indicated, oligonucleotides used in the following examples were prepared by synthesis using an automated synthesizer and were purified by gel electrophoresis or HPLC.

C-28 Thioxene:

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1N aqueous NaOH (2×), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr and stirred for another 30 min. The resulting mixture was poured into a mixture of ice water (800 mL) and ethyl acetate (250 mL). The organic phase was separated and the aqueous phase was extracted with ethyl acetate (3×). The combined organic phases were washed with $H_2O$ (2×), brine and were dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (LSIMS ($C_{42}H_{69}NO_2$): [M−H]$^+$ 618.6 $^1$H NMR (250 MHz, $CDCl_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCI(100 mL, 788 mmol). The reaction solution was heated at reflux for 23 hr under argon before being cooled to room temperature. To this was added additional TMSCI (50 mL, 394 mmol); and the reaction solution was heated at reflux for another 3 hr. The resulting solution was cooled and was made basic with cold 2.5N aqueous NaOH and was extracted with $CH_2Cl_2$ (3×). The combined organic layers were washed with saturated aqueous $NaHCO_3$ (2×) and brine, was dried over $Na_2SO_4$ and was concentrated in vacuo to give a brown oily liquid. Preparative column chromatography on silica gel by using a Waters 500 Prep LC system (gradient elution with hexane, 1:99, 2.98 ethyl acetate:hexane) provided 15.5 g (60%) of the C-28 thioxene as an orange-yellow oil (LSIMS ($C_{44}H_{71}NOS$): $[M-H]^+$ 661.6, $^1H$ NMR (250 MHz, $CDCl_3$) was consistent with the expected C-28 thioxene product 2-(4-(N,N-di-($C_{14}H_{29}$)-anilino)-3-phenyl thioxene.

Silicon tetra-t-butyl Phthalocyanine:

Sodium metal, freshly cut (5.0 g, 208 mmol), was added to 300 mL of anhydrous methanol in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr while the stream of ammonia gas continued during the course of the reaction, as solid started to precipitate. The resulting suspension was evaporated to dryness (house vacuum) and the residue was suspended in water (400 mL) and filtered. The solid was dried (60° C., house vacuum, $P_2O_6$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-L, round bottom flask and concentrated sulfuric acid (500 mL) was added with stirring. The mixture was stirred for 4 hr at 60° C. and was then carefully diluted with crushed Ice (2000 g). The resulting mixture was filtered and the solid was washed with 100 mL of water and dried. The dark blue solid was transferred to a 1-L, round bottom flask, concentrated ammonia (500 mL) was added, and the mixture was heated and stirred under reflux for 2 hr, was cooled to room temperature and was filtered. The solid was washed with 50 mL of water and dried under vacuum (house vacuum, 60° C., $P_2O_5$) to give 12 g of product silicon tetra-t-butyl phthalocyanine as a dark blue solid. 3-picoline (12 g, from Aldrich Chemical Co.), tri-n-butyl amine (anhydrous, 40 mL) and tri-n-hexyl chlorosilane (11.5 g) were added to 12 g of the above product in a one-liter, three-necked flask, equipped with a magnetic stirrer and a reflux condenser. The mixture was heated under reflux for 1.5 hr. and then cooled to room temperature. The picoline was distilled off under high vacuum (oil pump at about 1 mm Hg) to dryness. The residue was dissolved in $CH_2Cl_2$ and purified using a silica gel column (hexane) to give 10 g of pure product di-(tri-n-hexylsilyl)-silicon tetra-t-butyl phthalocyanine as a dark blue solid. (LSIMS: $[M-H]^+$ 1364.2, absorption spectra: methanol: 674 nm (□ 180,000): toluene 678 nm, $^1H$ NMR (250 MHz, $CDCl_3$): δ: −2.4(m, 12H), −1.3(m, 12H), 0.2–0.9 (m, 54H), 1.8(s, 36H), 8.3(d, 4H) and 9.6 (m, 8H) was consistent with the above expected product.

Sensitizer Beads Dyed with Silicon tetra-t-butyl Phthalocyanine

The sensitizer beads were prepared placing 600 mL of carboxylate modified beads (Seradyn) in a three-necked, round-bottom flask equipped with a mechanical stirrer, a glass stopper with a thermometer attached to it in one neck, and a funnel in the opposite neck. The flask had been immersed in an oil bath maintained at 94±1° C. The beads were added to the flask through the funnel in the neck and the bead container was rinsed with 830 mL of ethoxyethanol, 1700 mL of ethylene glycol and 60 mL of 0.1N NaOH and the rinse was added to the flask through the funnel. The funnel was replaced with a 24–40 rubber septum. The beads were stirred at 765 rpm at a temperature of 94±1° C. for 40 min.

Silicon tetra-t-butyl phthalocyanine (10.0 g) was dissolved in 300 mL of benzyl alcohol at 60±5° C. and 85 mL was added to the above round bottom flask through the septum by means of a syringe heated to 120±10° C. at a rate of 3 mL per min. The remaining 85 mL of the phthalocyanine solution was then added as described above. The syringe and flask originally containing the phthalocyanine was rinsed with 40 mL of benzyl alcohol and the rinse was transferred to the round-bottom flask. After 15 min 900 mL of deionized water and 75 mL of 0.1N NaOH was added dropwise over 40 min. The temperature of the oil bath was allowed to drop slowly to 40±10° C. and stirring was then discontinued. The bead were then filtered through a 43 micron polyester filter and subjected to a Microgon tangential flow filtration apparatus (Microgon Inc., Laguna Hills, Calif.) using ethanol:water, 100:0 to 10:90, and then filtered through a 43 micron polyester filter.

Hydroxypropylaminodextran

Hydroxypropylaminodextran ($1NH_2$/16 glucose) was prepared by dissolving Dextran T-500 (Pharmacia, Uppsala, Sweden) (100 g) in 500 mL of $H_2O$ in a 3-neck round-bottom flask equipped with mechanical stirrer and dropping funnel. To the above solution was added 45 g sodium hydroxide, 50 mg EDTA, 50 mg $NaBH_4$, 50 mg hydroquinone and 200 g N-(2,3-epoxypropyl) phthalimide. The mixture was heated and stirred in a 90° C. water bath for 2 hr. A small aliquot was precipitated three times from methanol and analyzed by NMR. Appearance of a peak at 7.3-7.6 6 indicated incorporation of phthalimide. The main reaction mixture was precipitated by addition to 3.5 L of methanol and the solid was collected. The phthalimide protecting group was removed by dissolving the product above in 500 mL of 0.1 M acetate buffer, adding 50 mL of 35% hydrazine and adjusting the pH to 3.5. The mixture was heated at 80° C. for 1 hr, the pH was readjusted to 3.2, and the mixture was heated for an additional one-half hour. An aliquot was precipitated three times in methanol. NMR showed that the phthalimide group was no longer present. The reaction mixture was neutralized to pH 8 and stored at room temperature.

The product was purified by tangential flow filtration using a 50,000 molecular weight cut-off filter, washing with about 8 L water, 0.5 L of 0.1M HCl, 0.5 L of 0.01 M NaOH, and finally 3 L of water. The product solution was concentrated by filtration to 700 mL and then was lyophilized. Determination of reactive amines using trinitrobenzene-sulfonate indicated about 1 amine per 16 glucose residues. Preparation of a second lot at twice the scale gave almost identical results.

Hydroxypropylaminodextran-coated Phthalocyanine Sensitizer Beads

A solution of hydroxypropylaminodextran (synthesized as described above) was prepared at 2 mg/mL in 50 mM MES (pH 6). One hundred fifty (150) mg phthalocyanine sensitizer beads in 7.5 mL water was added dropwise to 7.5 mL of the hydroxypropylaminodextran solution while vortexing. One hundred eighty eight (188) μL of EDAC solution (80 mg/mL) in water was added to the coating mixture while vortexing. The mixture was incubated overnight at room temperature in the dark. The mixture was diluted with 12 mL water and centrifuged. The supernatant was discarded and the bead pellet was suspended in 40 mL water by sonication. The beads were washed 3 times with water (40 mL per wash) by repeated centrifugation and suspension by sonication. The final pellet was suspended in 5 mL water.

Oligonucleotide Sensitizer Beads

Sixty five (65) mg of hydroxypropylaminodextran-coated phthalocyanine sensitizer beads (prepared as described above) were suspended in 5 mL 50 mM MOPS pH 7.A 10% (w/v) SIAX solution was prepared in DMSO and 77 μL was added to the bead suspension while vortexing. The mixture as incubated at room temperature for an additional 90 minutes in the dark and then a second 77 μL aliquot of SIAX solution was added and the mixture was incubated for an additional 60 minutes. The suspension was centrifuged and the supernatant was discarded. The bead pellet was suspended in 6 mL water by sonication and the centrifugation repeated. The pellet was suspended in 6.5 mL water and stored at 4° C.

In preparation for oligonucleotide coupling the beads were centrifuged, the supernatant was discarded and 1.34 mL coupling buffer was added to the pellet. Coupling buffer consists of the following mixture: 900 μL 0.2 M borate, 2 mM EDTA pH 9 and 333 μL of 0.4 M borate pH 9.45 and 1000 μL of 2 M sodium sulfate. The mixture was degassed and saturated with argon and then 9 μL of 10% Tween 20 detergent was added.

5'$A_{24}$ (SEQ Id NO:11) oligonucleotide modified at the 3' end with —$PO_2OCH_2CH_2CH_2SSCH_2CH_2CH_2OH$ was dissolved in water and the concentration was determined by optical density at 260 nm. Using the extinction coefficient supplied by the vendor, the concentration was found to be 915.8 nmoles/mL. Approximately twelve nmoles of oligonucleotide per mg of beads was used for the coupling procedure.

Seven hundred sixty (760) μL of oligonucleotide solution was placed in a centrifuge tube and 76 μL of 2.5 M sodium acetate pH 5.3 was added. One hundred forty seven (147) μL of 20 mM TCEP in water was added to the oligonucleotide solution and the mixture was incubated for one hr at room temperature in the dark. Four volumes of 200 proof ethanol was added to the mixture to precipitate the reduced oligonucleotide. Precipitation was facilitated by placing the mixture in a minus 20° C.-freezer for 1 hr. The precipitate was collected by centrifugation and then dissolved in 495 μL of 5 mM sodium hydrogen phosphate, 2 mM EDTA pH 6 that had been degassed and saturated with argon.

The oligonucleotide solution was then added to the bead pellet under coupling buffer and the mixture was sonicated to suspend the beads. The suspension was incubated at 37° C. for 23 hr. Residual iodo groups of the iodoaminodextran coat were capped by reaction with mercaptoacetic acid. The bead suspension was centrifuged and the supernatant was reserved. The pellet was suspended by sonication in 5 mL of 10 mM mercaptoacetic acid in 0.4 M borate pH 9.45 and the mixture was incubated at 37° C. for 1 hr. The beads were recovered by centrifugation and were suspended in 5 mL blocking buffer (0.1 M sodium chloride, 0.17 M glycine, 10 mg/mL BSA, 0.1% Tween 20, 1 mM EDTA pH 9.2, sterile filtered and 50 μL/mL Calf Thymus DNA, which was from Sigma, Cat. No. D8661 (10 mg/mL added). The mixture was incubated for 3 hr at 37° C. Following centrifugation the beads were washed twice by centrifugation with 5 mL of buffer (0.1 M Tris base, 0.3 M NaCl, 25 mM EDTA, 1 mg/mL Dextran T-500, 1 mg/mL BSA, 1:320 dilution of HBR-1, 0.05% Kathon, and 0.01 M gentamycin, pH 8.2) per wash. The final pellet was suspended in 6 mL IHBB (50 mM KCl, 10 mM Tris, 4 mM magnesium chloride, 0.02% acetylated BSA, pH 8.2) and was incubated at 95° C. for 90 min. After cooling the beads were centrifuged, the supernatant was discarded, and the pellet was suspended in 6 mL of equal volumes of 0.125 M sodium acetate pH 5 and 30% hydrogen peroxide solution. The mixture was incubated at 37° C. for 2.5 hr. The mixture was centrifuged, the supernatant was discarded and the beads were washed 3 times by centrifugation with storage buffer (50 mM KCI, 10 mM Tris, 4 mM EDTA, 0.02% acetylated BSA pH 8.2) using 5 mL buffer per wash. The final pellet was suspended by sonication in 6 mL storage buffer and was stored at 4° C. protected from light.

Chemiluminescer Acceptor Beads

A 10% solution of carboxylated latex beads (120 mL) was heated to 93° C. in a three-neck round bottom flask, and then was mixed with 166 mL ethoxyethanol, 336 mL ethylene glycol, and 12 mL of 0.1 M NaOH. A mechanical stirrer and a thermometer were added and the mixture was brought to 95° C. with stirring and then was stirred for an additional 40 min. In a separate flanks, 2.45 g of C-28 thioxene, 191.8 mg of 2-chloro-9-10-bis(phenylethynyl) anthracene, and 323.9 mg of rubrene were mixed in 264 mL of ethoxyethanol and the mixture was heated to 95° C. with stirring until dissolved. The dye solution was poured into the bead solution and was stirred for 20 min. at 95° C. and then was allowed to cool slowly to about 47° C. and filtered through a 43 micron polyester filter. The beads were washed by tangential flow filtration using a Microgon apparatus with a 0.05 micron filter. After priming of the system with wash solvent (1:2 v/v ethoxyethanol:ethylene glycol), the dyed bead mixture was added. The mixture was concentrated to about 20 mg/mL and then was washed with 6 L of wash solvent and 4.8 L of 10% v/v ethanol in water adjusted to pH 10 with NaOH. The beads were concentrated to about 50 mg/mL during the wash, and then were finally stored at 4° C. protected from light. Final concentration was determined by weight after evaporating an aliquot to dryness.

A plasticizer was incorporated into the beads to enhance the rate of decay of luminescence. A mixture was prepared containing 250 μL of n-heptadecylbenzene, 20 mL of ethanol and 0.5 g of hydroxypropylaminodextran dissolved in 25 mL of 50 mM MES pH 6. The mixture was heated to 80° C. in an oil bath and was stirred vigorously, but remained cloudy. A second mixture containing 40 mL of dyed beads from above (diluted to 25 mg/mL in 10% ethanol) and 30 mL of 50 mM MES pH 6 was also heated to 80° C. The two mixtures were combined and left stirring at 80° C. overnight.

After cooling, the beads were separated by a pipette from small pools of orange-colored n-heptadecylbenzene. EDAC (200 mg) in 3 mL of water was added and the mixture was stirred at room temperature for 2 hr and centrifuged to recover the beads. The pellet was washed with three 40 mL portions of water by centrifugation and then was resuspended in about 35 mL water.

Oligonucleotide Acceptor Beads

5'-(AGT AAG TAA GTA AGT AAG TAA GTA)-3' (SEQ ID NO:10) oligonucleotide modified at the 3' end with $—PO_2OCH_2CH_2CH_2SSCH_2CH_2CH_2OH$ was coupled to a 10 mg aliquot of the beads from above by reacting them with SIAX and thiolated oligonucleotide following essentially the same procedure as described above for the sensitizer beads. The only differences were the use of a lower ratio of oligonucleotide to beads (approximately 6 nmoles of oligonucleotide per mg beads) and omission of the hydrogen peroxide treatment step.

B. Commercially Purchased Reagents

Oligonucleotides were purchased from Oligos Etc. (Wilsonville, Oreg., USA). All oligonucleotides from Oligos Etc. were purified by gel electrophoresis, and oligonucleotides used as probes were chemically blocked at their 3'-ends. Tubes (Perkin Elmer, Norwalk, Conn., USA and ISC Bioexpress, Kaysville, Utah). *Chlamydia trachomatis* bacterial control DNA/RNA, LGV-II, strain 434 (ABI, Lot#08-901-000). Pfu/exo-polymerase was purchased from Stratagene, San Diego, Calif., USA).

C. Oligonucleotide Sequences Used for PCR Amplification and LOCI Detection of *Chlamydia trachomatis* DNA Amplified sequence (SEQ ID:1) (518 b.p.), nucleotides 2464-2981 of *Chlamydia trachomatis* cryptic plasmid pLGV440 (Genbank accession number X06707)

```
GGACAAATCGTATCTCGGGTTAATGTTGCATGATGCTTTATC

AAATGACAAGCTTAGATCCGTTTCTCATACGGTTTTCCTCGA

TGATTTGAGCGTGTGTAGCGCTGAAGAAAATTTGAGTAATTT

CATTTTCCGCTCGTTTAATGAGTACAATGAAAATCCATTGCG
TAGATCTCCGTTTCTATTGCTTGAGCGTATAAAGGGAAGGCT
TGACAGTGCTATAGCAAAGACTTTTTCTATTCGCAGCGCTAG
AGGCCGGTCTATTTATGATATATTCTCACAGTCAGAAATTGG
AGTGCTGGCTCGTATAAAAAAAAGACGAGCAACGTTCTCTG
AGAATCAAAATTCTTTCTTTGATGCCTTCCCAACAGGATACA
AGGATATTGATGATAAAGGAGTTATCTTAGCTAAAGGTAAT
TTCGTGATTATAGCAGCTAGGCCATCTATAGGGAAAACTGCT
TTAGCTATAGACATGGCGATAAATCTTGCGGTTACTCAACAG
CGTAGAGTTGGTTTCC
```

```
Forward primer (SEQ ID:2): 5'-GGA-CAA-ATC-GTA-TCT-CGG-GTT-
                           AAT-3'

Reverse primer (SEQ ID:3): 5'-GGA-AAC-CAA-CTC-TAC-GCT-GTT-3'

Probe SPI (SEQ ID:4):      5'-CGC-TGC-GAA-TAG-AAA-AAG-TCC-
                           ATT-TTT-TTT-TTT-TTT-TTT-TTT-X-3'

Probe DA1 (SEQ ID:5):      5'-CIC-TIC-IAA-TAI-AAA-AAI-TCC-ATT-
                           TTT-TTT-TTT-TTT-TTT-TTT-X-3'

Probe PN2 (SEQ ID:6):      5'-TAC-TTA-CTT-ACT-TAC-TTA-CTG-CCT-
                           AGC-TGC- TAT-AAT-CAC-GA-X-3'

Probe RL2 (SEQ ID:7):      5'-CTC-ACA-GTC-AGA-AAT-TGG-AG
                           (TACT)5-X-3'

Probe RL3 (SEQ ID:8):      5'-(T)20 AGA-CTT-TTT-CTA-TTC-GCA-GCG-
                           C-X-3'

Probe T02 (SEQ ID:9):      5'-(T)20 AIA-CTT-TTT-CTA-TTC-ICA-ICI-C-
                           X-3'
```

Oligonucleotides coupled to acceptor beads (SEQ ID:10): 5'-AGT-AAG-TAA-GTA-AGT-AAG-TAA-GTA-3'

Oligonucleotides coupled to sensitizer beads (SEQ ID:11): $dA_{24}$

X indicates that the oligonucleotide has been chemically blocked at the 3'-end (X=3'C-6 Amino).

D. Methods

1. LOCI Detection of PCR Amplification with LOCI Reagents in Amplification Reaction:

Forty-five microliters of a reaction mixture was prepared using concentrated stock solutions. The reaction mixture consisted of the following:

| Reagents | Final Conc. |
|---|---|
| IHBB | 1x |
| Pfu/exo- enzyme | 2.5 units |

-continued

| Reagents | Final Conc. |
|---|---|
| dNTPs | 200 µM |
| FWP | 250 nN4 |
| RevP | 250 nM |
| Probe SPI | 50 nM |
| Probe PN2 | 50 nM |
| DopTAR Acceptor beads | 2.5 µg |
| Sensitizer beads | 2.5 µg |

Forty-five microliters of the reaction mixture was aliquoted per reaction tube and either 5 µl water or 5 µl *Chlamydia trachomatis* DNA (different dilutions of a stock) was added. In addition, 20 µl mineral oil per individual tube was added.

a) PCR Amplification Followed by LOCI:

Cycling was performed in an Ericomp cycler (Ericomp, Inc., San Diego, Calif., USA) and the following cycling conditions were used:

| 95° C.: | 2.5 min | (1x) |
|---|---|---|
| 95° C.: | 15 sec | (40x) |
| 62° C.: | 1 min | (40x) |
| 74° C.: | 1 min | (40x) |
| 95° C.: | 2.5 min | (1 x) |
| 50° C.: | 15 min | (1x) |
| 37° C.: | 30 min | (1x) |

LOCI signals. were obtained by using the LOCI strip reader (Dade Behring Inc., Deerfield, Ill.). Immediately after amplification, samples were irradiated for 1 second and read for 1 second (3 cycles).

b) Real-time PCR/LOCI: Cycling was performed in a Biometra Uno thermalcycler (Biometra Inc., Tampa, Fla., USA) and the following cycling conditions were used:

| Reagents | Final Conc, |
|---|---|
| IHBB | 1x |
| Probe 1 | 50 nM |
| Probe 2 | 50 nM |
| DopTAR Acceptor beads | 2.5 µg |
| Sensitizer beads | 2.5 µg |

LOCI signals were obtained by using the LOCI strip reader (Dade Behring Inc., Deerfield, Ill.). Immediately after the incubation step at 37° C. the samples were irradiated for 0.1 seconds and read for 1 second (3 cycles) and the thermal cycler was put on hold. The strip-tubes were transferred back to the thermal cycler after irradiation/reading and thermocycling was resumed.

2. LOCI Assay (No Amplification) for Detection of PCR Amplified Targets by Adding LOCI Reagents after Amplification:

Forty-five microliters of a reaction mixture were prepared using concentrated stock solutions. The reaction mixture consisted of the following:

| 95° C.: | 2.5 min | (1x) |
|---|---|---|
| 95° C.: | 15 sec. | (40x) |
| 37° C.: | 2 min. | (40x) |
| 62° C.: | 1 min. | (40x) |
| 74° C.: | 1 min. | (40x) |

Note that Probes 1 and 2 correspond to SPI and PN2, respectively.

All the reagents were combined and either 5 µl water or 5 µl sample was added (final volume 50 µl). 20 µl of mineral oil was added to each tube. Samples were incubated at 95° C. for 15 seconds and at 37° C. for 2 minutes.

LOCI signals were obtained by using either the LOCI strip reader or the SPA/LOCI instrument (Dade Behring, Deerfield, Ill. Immediately after the incubation at 37° C., the samples were irradiated for 0.1 sec. and read for 1 sec. (3 cycles).

E. Assay Results

Real-time monitoring of PCR is based on kinetic measurements after every PCR cycle. In order to allow the DNA probes and beads to bind to the amplified target, an extra LOCI incubation step was added after every denaturation step in a standard PCR cycle. The conditions for the PCR amplification and real-time monitoring are described above. Surprisingly, a relatively short incubation step (37 C for 2 minutes) was sufficient to generate a LOCI signal.

The Dade Behring PCR/LOCI *Chlamydia trachomatis* (Dade Behring Inc., Deerfield, Ill.) assay was chosen as a model system. The results of a typical real-time monitoring PCR/LOCI experiment are shown in FIG. 1 (the raw data are depicted in Table 1 below). Different concentrations of a *Chlamydia trachomatis* stock (concentrations in elementary bodies/reaction) and a negative control (water) were evaluated.

The results indicate that LOCI can be used to monitor the PCR process. Surprisingly, no major changes regarding DNA probes, beads, primers etc. are necessary to use LOCI for real-time monitoring. Only an extra hybridization step had to be added to the normal PCR protocol to enable the successful monitoring of a PCR reaction. The higher the starting copy number of the DNA target, the sooner a significant increase in chemiluminescence is observed allowing quantitation over a wide range. Interestingly, the signal for a given target concentration first increases with increasing PCR cycle numbers, then reaches a plateau level and afterwards the signal decreases again.

Example 2

Quantitative Measurements Using Real-Time Monitoring of PCR and LOCI as the Detection Technology A. Standard Curve Generation The parameter Ct is defined as the cycle number at which the signal passes a fixed threshold above baseline. Quantitation of the amount of target in unknown samples is accomplished by measuring Ct and using a standard curve to determine the starting copy number.

Figure 2:
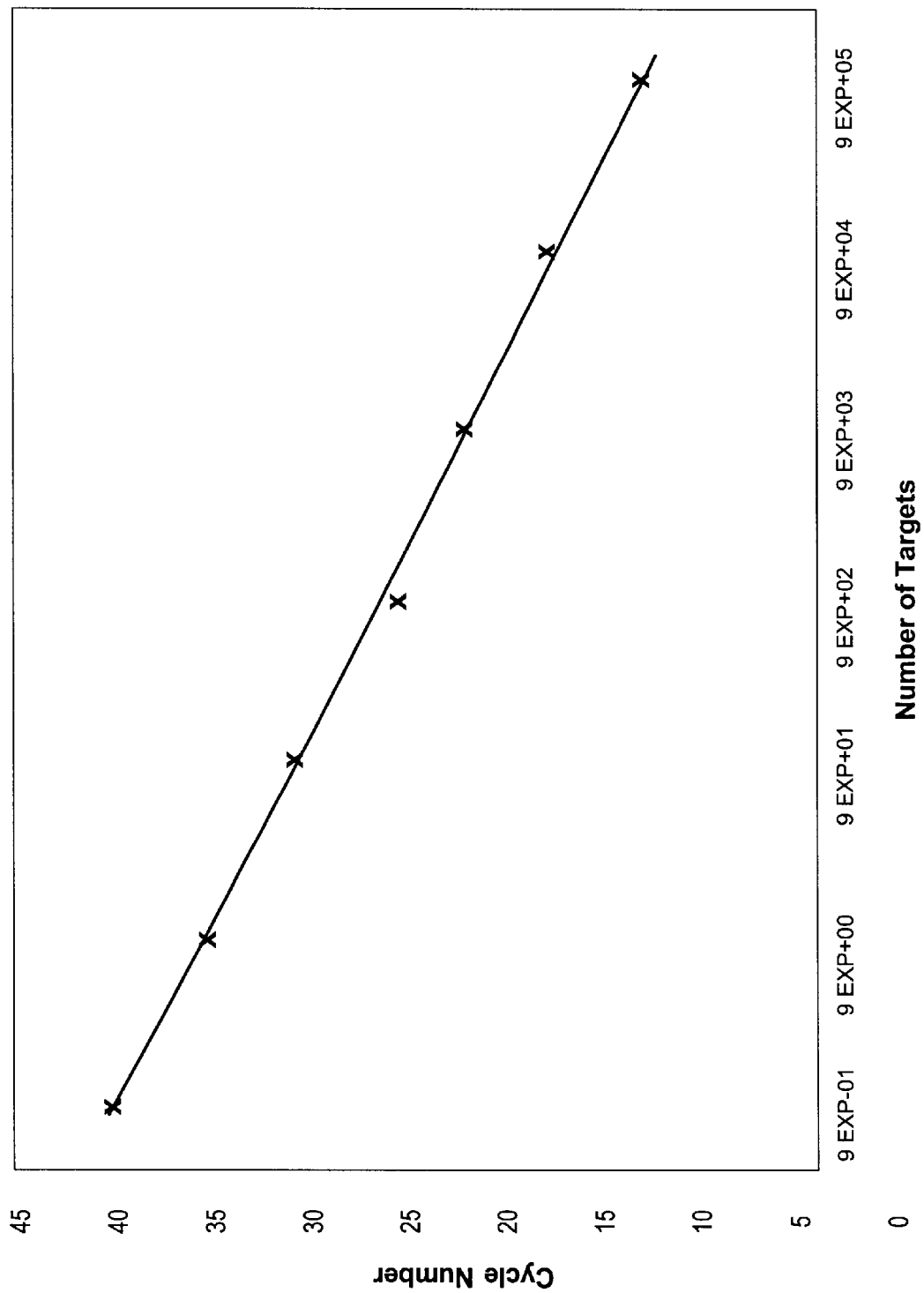
FIG. 2 is a standard curve for quantitation of the target DNA in an unknown sample generated using the real-time monitoring method of the current invention. The curve is plotted as cycle number vs. amount of target DNA.

FIG. 2 shows a typical standard curve, which allows quantitation of a target in an unknown sample. As illustrated by FIG. 2, real-time monitoring of PCR using LOCI offers a wide dynamic range (at least 6 orders of magnitude).

B. Imprecision

Figure 3:
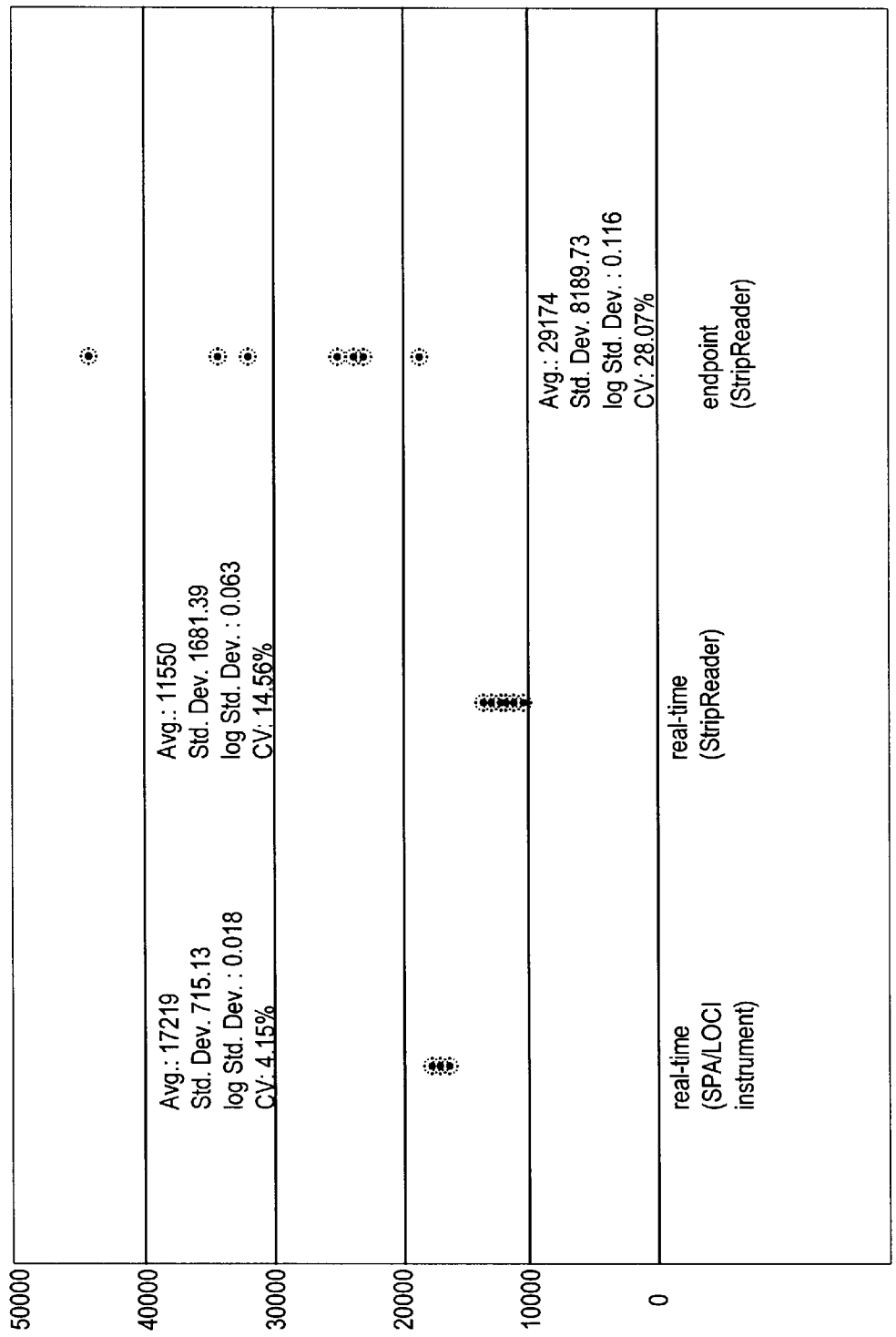
FIG. 3 is a plot showing interassay precision of light emission measurements comparing classical endpoint measurement and real-time monitoring using the current invention and the SPA/LOCI instrument or a strip reader.

Real-time monitoring is based on multiple measurements taken during the exponential phase of the PCR process. Since none of the reaction components is limited in the exponential phase, improved precision and accuracy can be expected. FIG. 3 shows a comparison of a classical endpoint measurement and two real-time monitoring experiments.

Eight replicates of a known *Chlamydia trachomatis* concentration ($9 \times 10^5$ EBs/reaction) were investigated.

The classical end-point measurement (40 PCR cycles plus one LOCI cycle) yielded the typical imprecision for an exponential amplification process. Real-time monitoring showed improved precision in comparison to end-point measurement. The SPA/LOCI instrument (Dade Behring, Deerfield, Ill.) showed the best precision data, probably because it required only 40 seconds to read all eight strip tubes, whereas the strip reader was much slower (approx. 2 min. for one strip).

C. High-Dose Hook Effect

Figure 4:
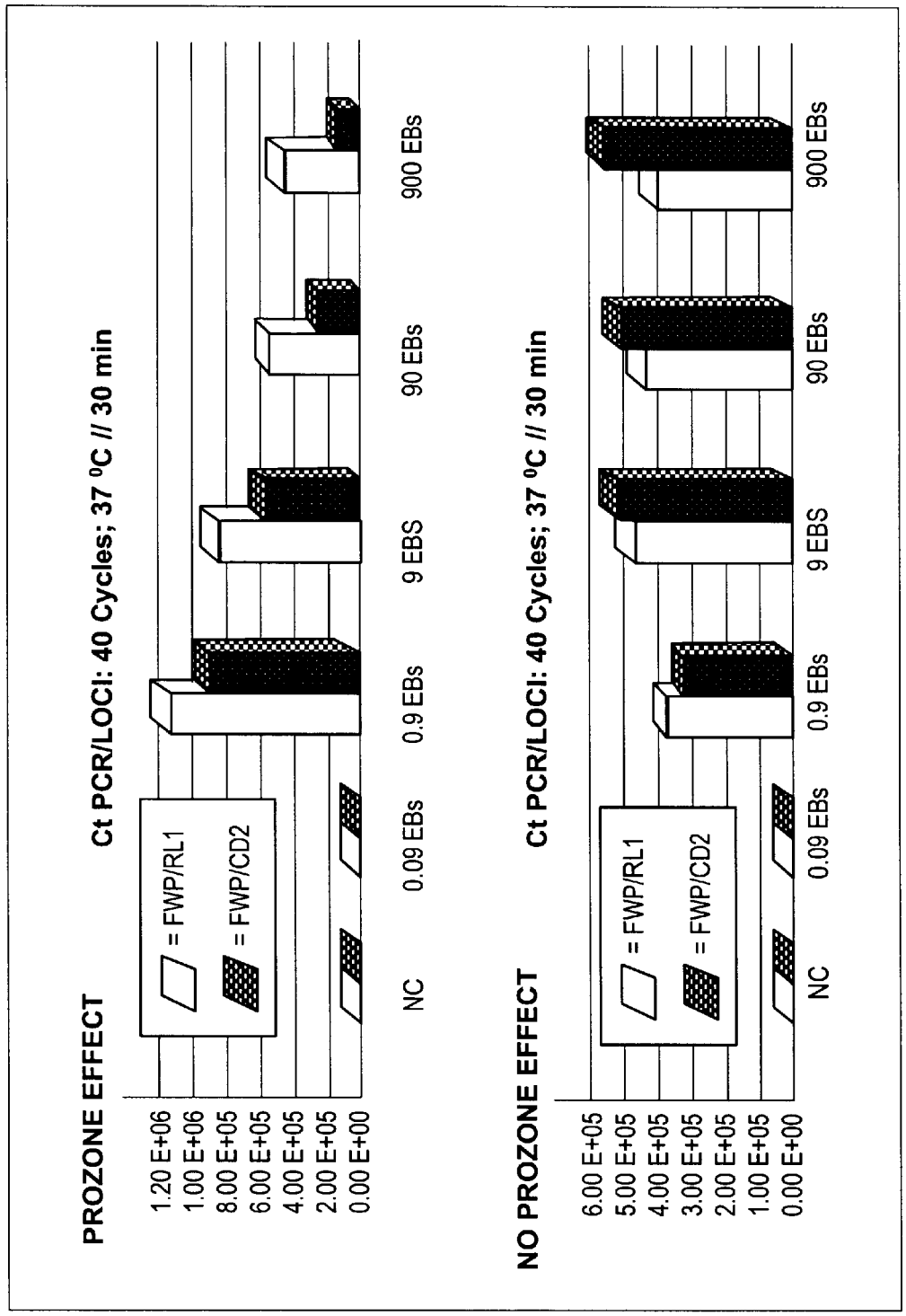
FIG. 4 is a plot of light emission versus amount of DNA in elementary bodies (EBs) including high concentrations of DNA which elicit a hook effect with standard LOCI endpoint measurements. There are about 10 DNA targets (cryptic plasmids) per elementary body ("EB"). Hence, 0.9 EB is approximately equivalent to 9 DNA targets.

It was previously observed that the Ct PCR/LOCI assay is prone to a high-dose hook effect because the amount of amplified target exceeds the amount of DNA probes and beads. No high-dose hook effect was observed using real-time monitoring, probably because DNA probes and beads have only a very short time (2 min. in real-time monitoring vs. 30 min. in classical end-point measurements) to bind to their targets (FIG. 4). Similar results were obtained using different primer combinations which generated a longer (approximately 500 bps with FWP CD2) and a shorter amplicon (approximately 250 bps with FWP RLI).

D. Specificity

The real-time monitoring protocol described in the Examples above, contains an extra incubation step (37 C/2min,) for each PCR cycle allowing the DNA probes and beads to bind to their targets. It is well known that at low temperatures, primers can bind to unspecific regions causing a variety of undesired effects. Therefore, non-specific binding was analyzed.

Figure 5:
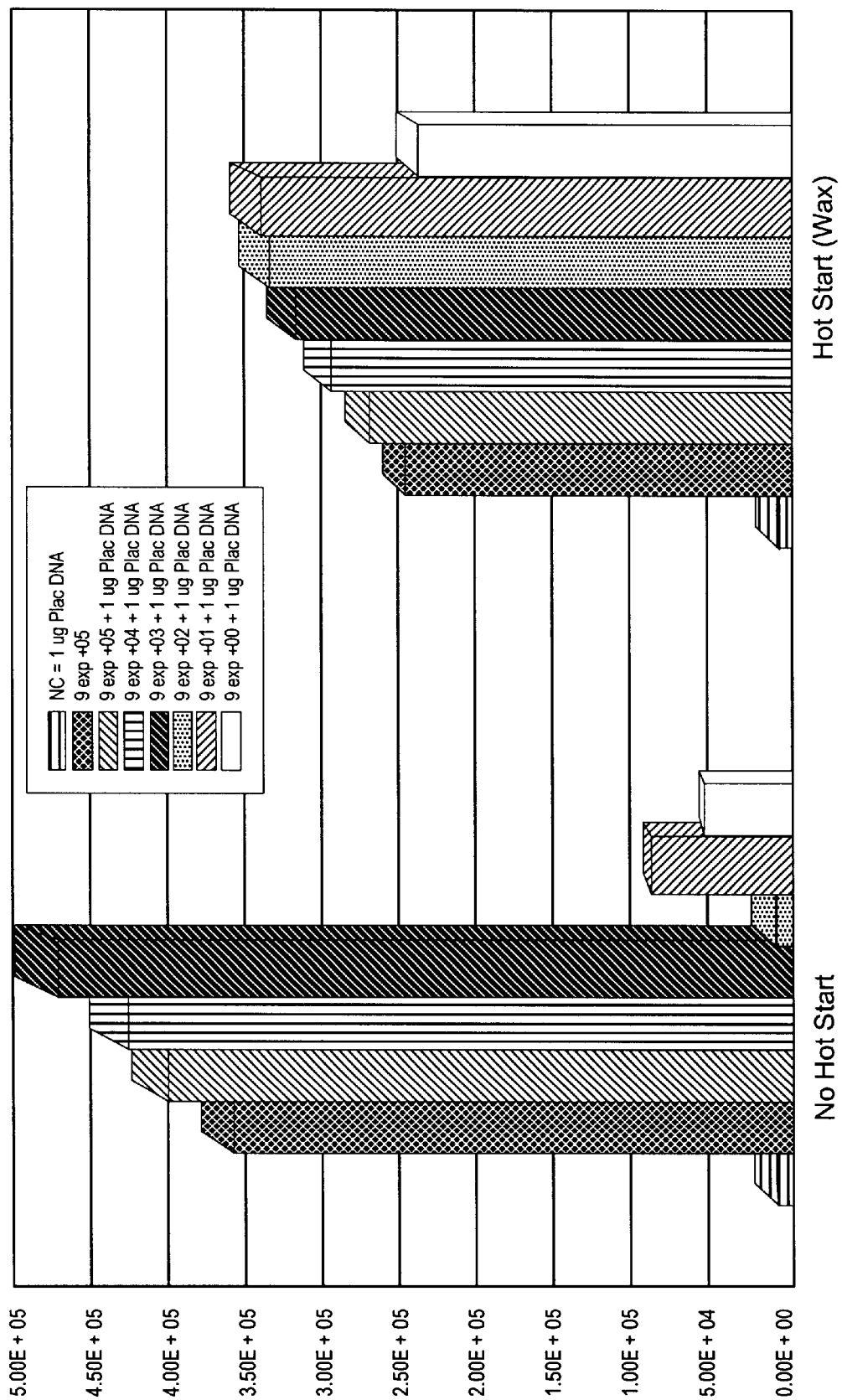
FIG. 5 is a plot of light emission versus amount of specific and non-specific DNA with and without hot start (wax).

FIG. 5 shows the effect of unspecific DNA (1 μg Placenta DNA) on the amplification efficiency using real-time monitoring conditions. Different dilutions of Ct target in the absence or presence of unspecific DNA with and without wax beads were evaluated. Without wax beads impaired amplification efficiency at low target concentrations was observed in the presence of unspecific DNA. When wax beads were used the presence of unspecific DNA had no negative effect on amplification efficiency at high and low target concentrations. The incubation step at 37 C had no negative impact on amplification efficiency.

Figure 6:
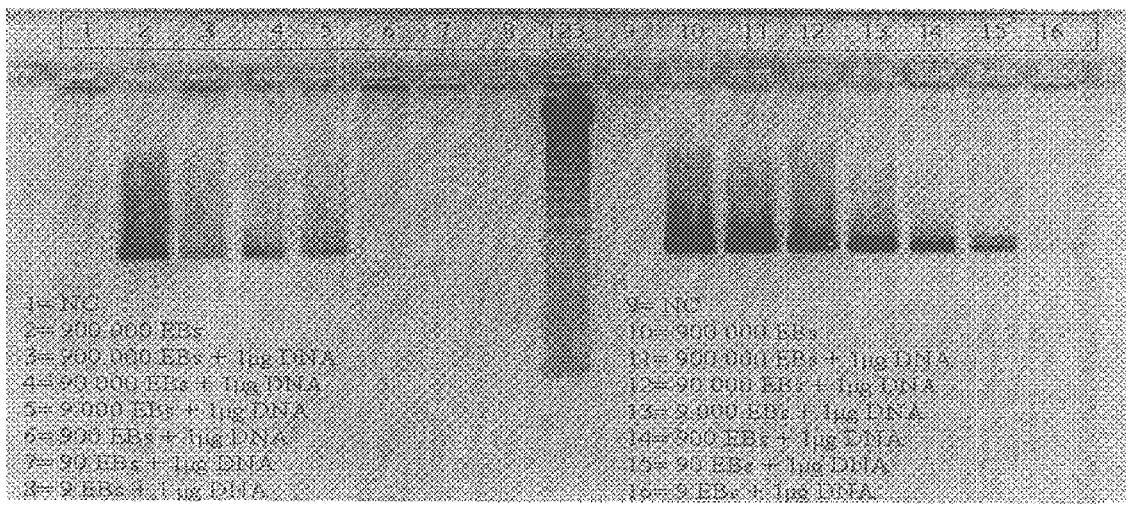
FIG. 6 is a digitized image of an EtBr-stained agarose gel under UV light after electrophoresis of products of the PCR reaction with real-time monitoring using LOCI according to the current invention with varying concentrations of target and unspecific DNA and with and without a hot start. The product of the PCR amplification has an expected size of 518 base pairs which corresponds to the predicted size of the major band in the sample lanes.

EtBr-stained agarose gel electrophoresis (FIG. 6) confirmed the above-mentioned conclusions based on LOCI results by revealing a single band of the expected size, approximately 500 bps, for the PCR product generated with added unspecific DNA for as low as 9 EBs with wax beads (hot start) as opposed to 900 Ebs without wax beads.

Figure 7:
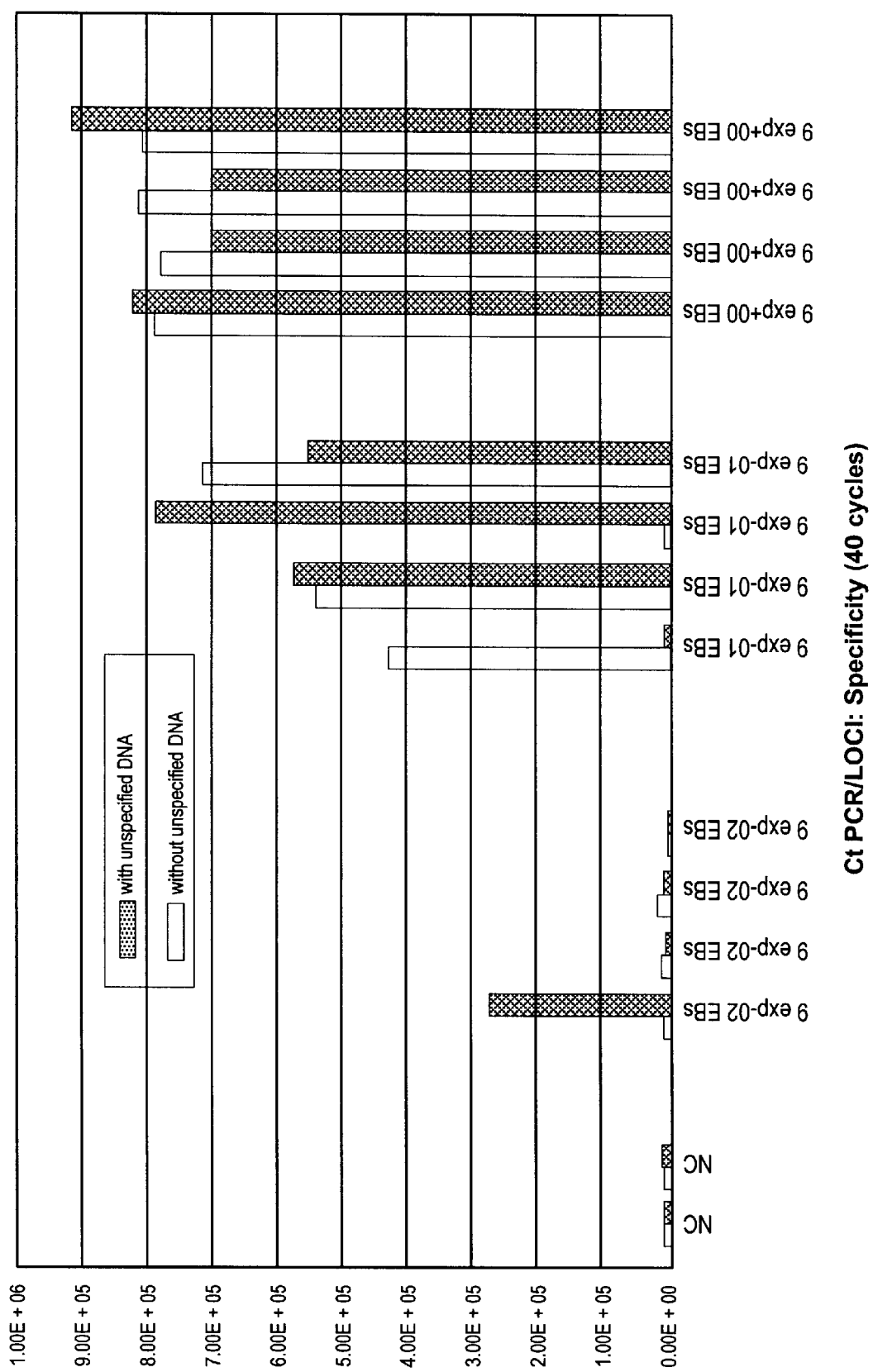
FIG. 7 is a graph of light emission of replicates various experimental groups with varying amounts of target DNA, with and without unspecific DNA.

FIG. 7 depicts a similar experiment showing the results at the sensitivity limit of the assay, 0.9 EBs/reaction) with and without unspecific DNA. No negative side effects were observed using an extra incubation step at 37 C during each PCR cycle. Note that dilutions of Ebs to $9 \times 10^{-2}$ and $9 \times 10^{-1}$ represents about 0 to 10 DNA targets. Therefore, this bar graph represents acceptable sensitivity for Chlamydia cryptic plasmid DNA targets.

Example 3

Deleterious Effects of Singlet Oxygen

It was shown in a number of experiments (data not shown) that singlet oxygen or radicals destroy or modify the DNA probe binding to the sensitizer beads. There is evidence from the literature that guanine is very vulnerable to singlet oxygen and radicals. Therefore, guanosine residues in the probe binding to sensitizer beads were substituted by either de-aza-guanosine residues or inosine residues.

A mixture of Ct amplicon (the amplified Chlamydia product) or water, LOCI beads and DNA probes were incubated (95 C/15 sec. and 37 C/2 min.) and irradiated and read ((0.1 sec irr./1 sec. read) 3×). These steps were repeated 20 time for a total of 20 cycles. The guanosine-containing probe SPI shows a decline in signal after multiple incubation/irradiation/reading cycles. The inosine-containing probe DAI shows no significant decline in signal after multiple incubation/radiation/reading cycles. However, DAI is not as sensitive as SPI. The de-aza-guanosine-containing probe (data not shown) is even more vulnerable to singlet oxygen than SPI.

Figure 8:
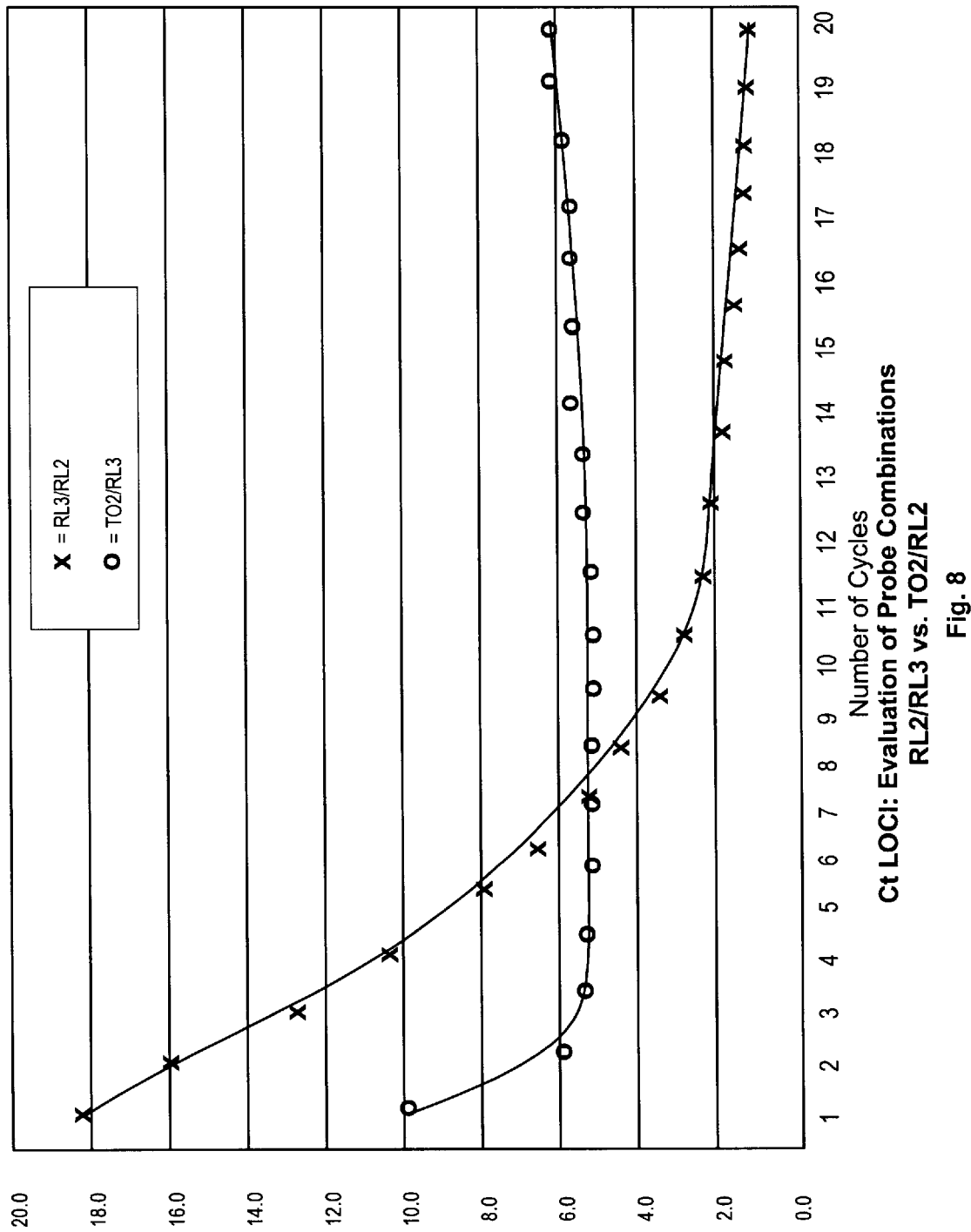
FIG. 8 is a plot of denaturation/annealing/irradiation cycle numbers versus ratios of the emission generated from LOCI using a sensitizer probe that contains guanosine (RL3) or inosine (TO2). The ratios on the Y-axis are calculated by dividing the relative light units ("RLU") of a DNA target blank (no DNA amplicon).

FIG. 8 shows another comparison of a guanosine-containing sensitizer probe (RL3) and an inosine-containing sensitizer probe (TO2) confirming the above-mentioned conclusions that inosine-containing probes are less sensitive to multiple irradiations than guanosine containing probes.

Although the foregoing invention has been described in some detail by way of illustration and example for purposes of clarity and understanding, it will be obvious that certain changes or modifications may be practiced within the scope of the appended claims.

What is claimed:

1. A method for detecting the presence of a target polynucleotide in a sample comprising:
   (A) providing a reaction and detection mixture comprising in combination:
      (1) a sample;
      (2) a nucleic acid amplification system; and
      (3) a chemiluminescent detection system comprising a sensitizer capable of indirectly binding to the target polynucleotide and capable of generating singlet oxygen upon irradiation with light and a singlet-oxygen activatable chemiluminescent compound capable of indirectly binding to the amplified target nucleic acid;
   (B) amplifying said target polynucleotide through at least one amplification cycle;
   (C) allowing the indirect binding of said chemiluminescent compound and said sensitizer to said amplified target polynucleotide;
   (D) activating the sensitizer, wherein said activation of the sensitizer bound to the target polynucleotide causes the activation of said chemiluminescent compound bound to the target polynucleotide;
   (E) determining the amount of luminescence generated by the activated chemiluminescent compound;
   (F) optionally repeating steps B–E; and
   (G) detecting the presence of said target polynucleotide by analyzing the amount of luminescence determined after at least one amplification cycle.

2. The method of claim 1 wherein the sensitizer is a photosensitizer and the activation of the sensitizer comprises irradiation with light.

3. The method of claim 2 wherein:
   (A) the target polynucleotide comprises a first and a second complimentary strand; and
   (B) the nucleic acid amplification system comprises:
      (1) a thermostable DNA polymerase;
      (2) 2' deoxynucleoside-5'-triphosphates;
      (3) a forward-primer capable of binding to the first complimentary strand; and
      (4) a reverse-primer capable of binding to the second complimentary strand in a position that will direct DNA synthesis toward the site of annealing of the forward-priming oligonucleotide.

4. The method of claim 3 wherein:
   (A) the chemiluminescent detection system further comprises:
      (i) a first linking oligonucleotide capable of binding to both the target polynucleotide and a chemiluminescer-associated oligonucleotide; and
      (ii) a second linking oligonucleotide capable of binding to both the target polynucleotide and a sensitizer-associated oligonucleotide;
   (B) the sensitizer and sensitizer-associated oligonucleotide are associated with a first solid support;
   (C) the singlet-oxygen activatable chemiluminescent compound and the chemiluminescer-associated oligonucleotide are associated with a second solid support.

5. The method of claim 4 wherein the nucleic acid amplification system is the polymerase chain reaction.

6. The method of claim 5 wherein the first and second solid support are beads and the acceptor beads comprise thioxene, anthracene, and rubrene.

7. The method of claim 6 wherein the amplification system further includes a thermal labile antibody against the thermal stable DNA polymerase.

8. The method of claim 5 wherein the target polynucleotide is from *Chlamydia trachomatis*.

9. The method of claim 5 wherein guanosine residues are replaced with inosine residues in one or both of the first and second linking probes.

10. The method of claim 5 wherein said luminescence determinations are made during an exponential phase of the amplification process.

11. The method of claim 5 wherein the method is used to determine the quantity of said target polynucleotide in a sample, said method further comprises:
    (A) determining a threshold cycle number at which the luminescence generated from amplification of the target polynucleotide in a sample reaches a fixed threshold value above a baseline value; and
    (B) calculating the quantity of the target polynucleotide in the sample by comparing the threshold cycle number determined for the target polynucleotide in a sample with the threshold cycle number determined for target polynucleotides of known amounts in standard solutions.

12. A method for detecting the presence of a target polynucleotide in a sample, the target polynucleotide comprising a first and a second complimentary strand, said method comprising:
    (A) providing a reaction and detection mixture comprising in combination:
       (1) a sample,
       (2) a thermostable DNA polymerase,
       (3) 2' deoxynucleoside-5'-triphosphates,
       (4) a forward-primer capable of binding to the first complimentary strand,
       (5) a reverse-primer capable of binding to the second complimentary strand in a position that will direct DNA synthesis toward the site of annealing of the forward-priming oligonuceotide, and
       (6) a chemiluminescent detection system comprising a photosensitizer capable of indirectly binding to the target polynucleotide and capable of generating singlet oxygen upon irradiation with light and a singlet-oxygen activatable chemiluminescent compound capable of indirectly binding to the amplified target nucleic acid;
    (B) denaturing said target polynucleotide for an initial denaturation period;
    (C) denaturing said target polynucleotide for a cycle denaturation period;
    (D) incubating the reaction and detection mixture to allow indirect binding of said chemiluminescent compound and said photosensitizer to said amplified target polynucleotide;
    (E) irradiating the photosensitizer with light, wherein said irradiation causes the activation of said chemiluminescent compound bound to the target polynucleotide by the sensitizer bound to the target polynucleotide; and
    (F) determining the amount of luminescence generated by the activated chemiluminescent compound;
    (G) annealing said forward priming and reverse priming oligonucleotides to the target polynucleotide;
    (H) synthesizing polynucleotide strands complementary to said first and second complementary strands of said target polynucleotide, said synthesis being catalyzed by the thermostable DNA polymerase;
    (I) optionally repeating steps C–H; and
    (J) detecting the presence of said target polynucleotide by analyzing the amount of luminescence determined after at least one amplification cycle.

13. The method of claim 12 wherein:
(A) the chemiluminescent detection system further comprises:
  (i) a first linking oligonucleotide capable of binding to both the target polynucleotide and a chemiluminescer-associated oligonucleotide; and
  (ii) a second linking oligonucleotide capable of binding to both the target polynucleotide and a sensitizer-associated oligonucleotide.
(B) the sensitizer and sensitizer-associated oligonucleotide are associated with a first solid support; and
(C) the singlet-oxygen activatable chemiluminescent compound and the chemiluminescer-associated oligonucleotide are associated with a second solid support.

14. The method of claim 13 wherein the nucleic acid amplification system is the polymerase chain reaction.

15. The method of claim 14 wherein the first and second solid support are beads and the acceptor beads comprise thioxene, anthracene, and rubrene.

16. The method of claim 15 wherein the amplification system further includes a thermal labile antibody against the thermal stable DNA polymerase.

17. The method of claim 14 wherein the target polynucleotide is from *Chlamydia trachomatis*.

18. The method of claim 14 wherein guanosine residues are replaced with inosine residues in one or both of the first and second linking probes.

19. The method of claim 14 wherein said luminescence determinations are made during an exponential phase of the amplification process.

20. The method of claim 14 wherein the method is used to determine the quantity of said target polynucleotide in a sample, said method further comprising:
(A) determining a threshold cycle number at which the luminescence generated from amplification of the target polynucleotide in a sample reaches a fixed threshold value above a baseline value;
(B) calculating the quantity of the target polynucleotide in the sample by comparing the threshold cycle number determined for the target polynucleotide in a sample with the threshold cycle number determined for target polynucleotides of known amounts in standard solutions.

* * * * *